US011779460B2

(12) United States Patent
Desrosiers

(10) Patent No.: US 11,779,460 B2
(45) Date of Patent: Oct. 10, 2023

(54) METHODS FOR CONTROLLED HEART VALVE DELIVERY

(71) Applicant: Edwards Lifesciences Corporation, Irvine, CA (US)

(72) Inventor: John J. Desrosiers, San Clemente, CA (US)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 172 days.

(21) Appl. No.: 17/347,446

(22) Filed: Jun. 14, 2021

(65) Prior Publication Data

US 2021/0307899 A1 Oct. 7, 2021

Related U.S. Application Data

(63) Continuation of application No. 16/378,307, filed on Apr. 8, 2019, now Pat. No. 11,033,387, which is a
(Continued)

(51) Int. Cl.
A61F 2/24 (2006.01)

(52) U.S. Cl.
CPC ............ A61F 2/243 (2013.01); A61F 2/2418 (2013.01); A61F 2/2436 (2013.01); A61F 2220/0033 (2013.01)

(58) Field of Classification Search
CPC ...... A61F 2/243; A61F 2/2436; A61F 2/2439; A61F 2/2427; A61F 2/962; A61F 2/966; A61F 2002/9505; A61F 2002/9534; A61F 2002/9528; A61F 2002/9511; A61F 2220/0033; A61F 2220/0083; A61B 17/221
See application file for complete search history.

(56) References Cited

U.S. PATENT DOCUMENTS 4,592,340 A 6/1986 Boyles
4,994,077 A 2/1991 Dobben
(Continued)

FOREIGN PATENT DOCUMENTS

CA 2767527 A1 1/2011
CN 101953725 A 1/2011
(Continued)

Primary Examiner — Diane D Yabut
(74) Attorney, Agent, or Firm — Brandon J. Johnson; Klarquist Sparkman, LLP

(57) ABSTRACT

A prosthetic implant delivery assembly includes a prosthetic implant including an expandable stent and a catheter for delivering the prosthetic implant. The expandable stent includes apices circumferentially-spaced apart relative to each other. At least some of the apices include an aperture disposed therein. The catheter includes arms disposed at an end of a shaft, and the arms are moveable between a radially compressed state and a radially expanded state via a sheath. The arms each include a hook portion for releasably engaging the apertures of the apices. The arms are configured to move from the radially compressed state to the radially expanded state when the plurality arms is exposed from within the sheath such that the hook portion disengages from the apices of the prosthetic implant and releases the expandable stent from the catheter.

19 Claims, 12 Drawing Sheets

Related U.S. Application Data continuation of application No. 15/351,823, filed on Nov. 15, 2016, now Pat. No. 10,265,169.

(60) Provisional application No. 62/258,973, filed on Nov. 23, 2015.

(56) References Cited

U.S. PATENT DOCUMENTS

| | | | |
|---|---|---|---|
| 5,059,177 A | 10/1991 | Towne | |
| 5,411,552 A | 5/1995 | Andersen et al. | |
| 5,554,185 A | 9/1996 | Block et al. | |
| 5,591,195 A | 1/1997 | Taheri et al. | |
| 5,599,305 A | 2/1997 | Hermann et al. | |
| 5,639,274 A | 6/1997 | Fischell et al. | |
| 5,728,068 A | 3/1998 | Leone et al. | |
| 5,840,081 A | 11/1998 | Andersen et al. | |
| 5,968,068 A | 10/1999 | Dehdashtian et al. | |
| 6,040,416 A | 3/2000 | Sekharipuram et al. | |
| 6,168,614 B1 | 1/2001 | Andersen et al. | |
| 6,217,585 B1 | 4/2001 | Houser et al. | |
| 6,379,372 B1 | 4/2002 | Dehdashtian et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,527,979 B2 | 3/2003 | Constantz et al. | |
| 6,582,462 B1 | 6/2003 | Andersen et al. | |
| 6,652,578 B2 | 11/2003 | Bailey et al. | |
| 6,679,893 B1 * | 1/2004 | Tran | A61B 17/221 606/127 |
| 6,730,118 B2 | 5/2004 | Spenser et al. | |
| 6,733,525 B2 | 5/2004 | Yang et al. | |
| 6,767,362 B2 | 7/2004 | Schreck | |
| 6,830,584 B1 | 12/2004 | Seguin | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,018,408 B2 | 3/2006 | Bailey et al. | |
| 7,276,084 B2 | 10/2007 | Yang et al. | |
| 7,318,278 B2 | 1/2008 | Zhang et al. | |
| 7,374,571 B2 | 5/2008 | Pease et al. | |
| 7,393,360 B2 | 7/2008 | Spenser et al. | |
| 7,510,575 B2 | 3/2009 | Spenser et al. | |
| 7,585,321 B2 | 9/2009 | Cribier | |
| 7,618,446 B2 | 11/2009 | Andersen et al. | |
| 7,749,266 B2 | 7/2010 | Forster et al. | |
| 7,780,726 B2 | 8/2010 | Seguin | |
| 7,785,366 B2 | 8/2010 | Maurer et al. | |
| 7,959,661 B2 | 6/2011 | Hijlkema et al. | |
| 7,993,394 B2 | 8/2011 | Hariton et al. | |
| 8,029,556 B2 | 10/2011 | Rowe | |
| 8,167,932 B2 | 5/2012 | Bourang et al. | |
| 8,182,530 B2 | 5/2012 | Huber | |
| 8,449,606 B2 | 5/2013 | Eliasen et al. | |
| 8,652,145 B2 | 2/2014 | Maimon et al. | |
| 8,652,202 B2 | 2/2014 | Alon et al. | |
| 8,801,776 B2 | 8/2014 | House et al. | |
| 9,119,717 B2 | 9/2015 | Wang et al. | |
| 9,155,619 B2 | 10/2015 | Liu et al. | |
| 9,168,131 B2 | 10/2015 | Yohanan et al. | |
| 9,180,005 B1 | 11/2015 | Lashinski et al. | |
| 9,867,700 B2 | 1/2018 | Bakis et al. | |
| 2002/0032481 A1 | 3/2002 | Gabbay | |
| 2002/0151970 A1 | 10/2002 | Garrison et al. | |
| 2002/0161377 A1 | 10/2002 | Rabkin | |
| 2003/0040792 A1 | 2/2003 | Gabbay | |
| 2003/0050694 A1 | 3/2003 | Yang et al. | |
| 2004/0133263 A1 | 7/2004 | Dusbabek et al. | |
| 2004/0186563 A1 | 9/2004 | Lobbi | |
| 2004/0186565 A1 | 9/2004 | Schreck | |
| 2004/0210304 A1 | 10/2004 | Seguin et al. | |
| 2004/0236411 A1 | 11/2004 | Sarac et al. | |
| 2004/0260389 A1 | 12/2004 | Case et al. | |
| 2005/0075731 A1 | 4/2005 | Artof et al. | |
| 2005/0080474 A1 | 4/2005 | Andreas et al. | |
| 2005/0096736 A1 | 5/2005 | Osse et al. | |
| 2005/0113910 A1 | 5/2005 | Paniagua et al. | |
| 2005/0137688 A1 | 6/2005 | Salahieh et al. | |
| 2005/0137693 A1 | 6/2005 | Haug et al. | |
| 2005/0137697 A1 | 6/2005 | Salahieh et al. | |
| 2005/0143809 A1 | 6/2005 | Salahieh et al. | |
| 2005/0149159 A1 | 7/2005 | Andreas et al. | |
| 2005/0149160 A1 | 7/2005 | McFerran | |
| 2005/0203614 A1 | 9/2005 | Forster et al. | |
| 2005/0203617 A1 | 9/2005 | Forster et al. | |
| 2006/0025857 A1 | 2/2006 | Bergheim et al. | |
| 2006/0149360 A1 | 7/2006 | Schwammenthal et al. | |
| 2006/0167487 A1 | 7/2006 | Hamada | |
| 2006/0259136 A1 | 11/2006 | Nguyen et al. | |
| 2006/0276813 A1 | 12/2006 | Greenberg | |
| 2006/0287719 A1 | 12/2006 | Rowe et al. | |
| 2007/0005131 A1 | 1/2007 | Taylor | |
| 2007/0073389 A1 | 3/2007 | Bolduc et al. | |
| 2007/0088431 A1 | 4/2007 | Bourang et al. | |
| 2007/0203575 A1 | 8/2007 | Forster et al. | |
| 2007/0213813 A1 | 9/2007 | Von Segesser et al. | |
| 2007/0265700 A1 | 11/2007 | Eliasen et al. | |
| 2008/0125853 A1 | 5/2008 | Bailey et al. | |
| 2008/0262592 A1 | 10/2008 | Jordan et al. | |
| 2008/0294230 A1 | 11/2008 | Parker | |
| 2008/0319526 A1 | 12/2008 | Hill et al. | |
| 2009/0099638 A1 | 4/2009 | Grewe | |
| 2009/0157175 A1 | 6/2009 | Benichou | |
| 2009/0276040 A1 | 11/2009 | Rowe et al. | |
| 2009/0281619 A1 | 11/2009 | Le et al. | |
| 2009/0319037 A1 | 12/2009 | Rowe et al. | |
| 2010/0049313 A1 | 2/2010 | Alon et al. | |
| 2010/0191326 A1 | 7/2010 | Alkhatib | |
| 2010/0198347 A1 | 8/2010 | Zakay et al. | |
| 2011/0015729 A1 | 1/2011 | Jimenez et al. | |
| 2011/0040374 A1 | 2/2011 | Goetz et al. | |
| 2011/0264191 A1 | 10/2011 | Rothstein | |
| 2012/0071969 A1 | 3/2012 | Li et al. | |
| 2012/0123529 A1 | 5/2012 | Levi et al. | |
| 2013/0310923 A1 | 11/2013 | Kheradvar et al. | |
| 2013/0317598 A1 | 11/2013 | Rowe et al. | |
| 2014/0067037 A1 | 3/2014 | Fargahi | |
| 2015/0157455 A1 | 6/2015 | Hoang et al. | |
| 2015/0173897 A1 | 6/2015 | Raanani et al. | |
| 2017/0056149 A1 | 3/2017 | Rajpara et al. | |
| 2017/0128197 A1 | 5/2017 | Bialas et al. | |
| 2017/0156839 A1 | 6/2017 | Cooper et al. | |
| 2017/0156859 A1 | 6/2017 | Chang et al. | |
| 2017/0231765 A1 | 8/2017 | Desrosiers et al. | |
| 2017/0258584 A1 | 9/2017 | Chang et al. | |

FOREIGN PATENT DOCUMENTS

| | | |
|---|---|---|
| DE | 19532846 A1 | 3/1997 |
| DE | 19907646 A1 | 8/2000 |
| EP | 0592410 B1 | 10/1995 |
| EP | 0850607 A1 | 7/1998 |
| EP | 1796597 A2 | 6/2007 |
| EP | 2218403 A1 | 8/2010 |
| EP | 3028668 A1 | 6/2016 |
| FR | 2815844 A1 | 5/2002 |
| WO | 9117720 A1 | 11/1991 |
| WO | 9829057 A1 | 7/1998 |
| WO | 0041652 A1 | 7/2000 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 03047468 A1 | 6/2003 |
| WO | 2005084595 A1 | 9/2005 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2008124844 A1 | 10/2008 |
| WO | 2010022138 A2 | 2/2010 |

(56) References Cited

FOREIGN PATENT DOCUMENTS

| WO | 2010121076 A2 | 10/2010 |
|---|---|---|
| WO | 2010130297 A1 | 11/2010 |
| WO | 2011133792 A1 | 10/2011 |
| WO | 2012150290 A1 | 11/2012 |
| WO | 2013175468 A2 | 11/2013 |
| WO | 2014081796 A1 | 5/2014 |

* cited by examiner

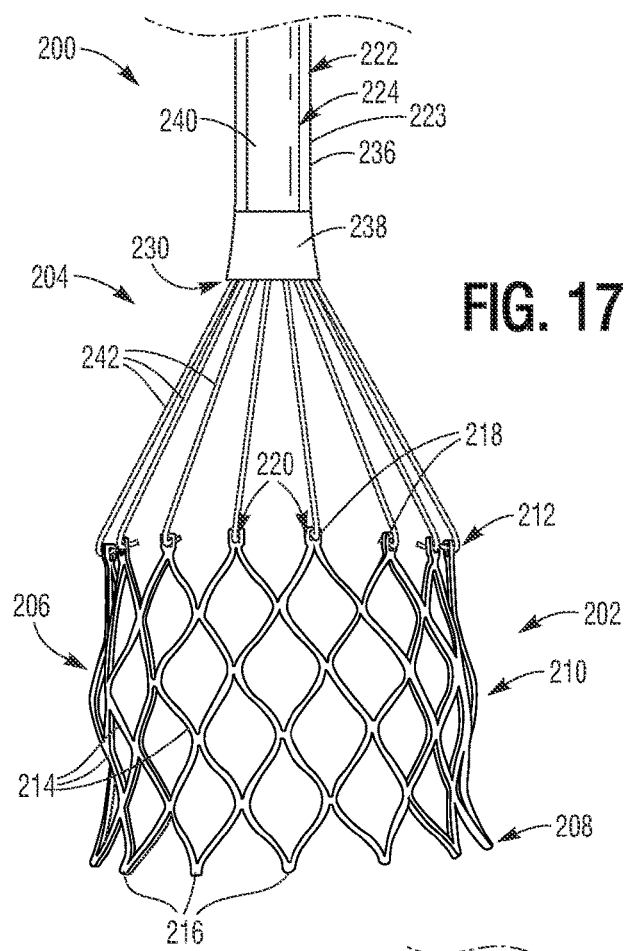
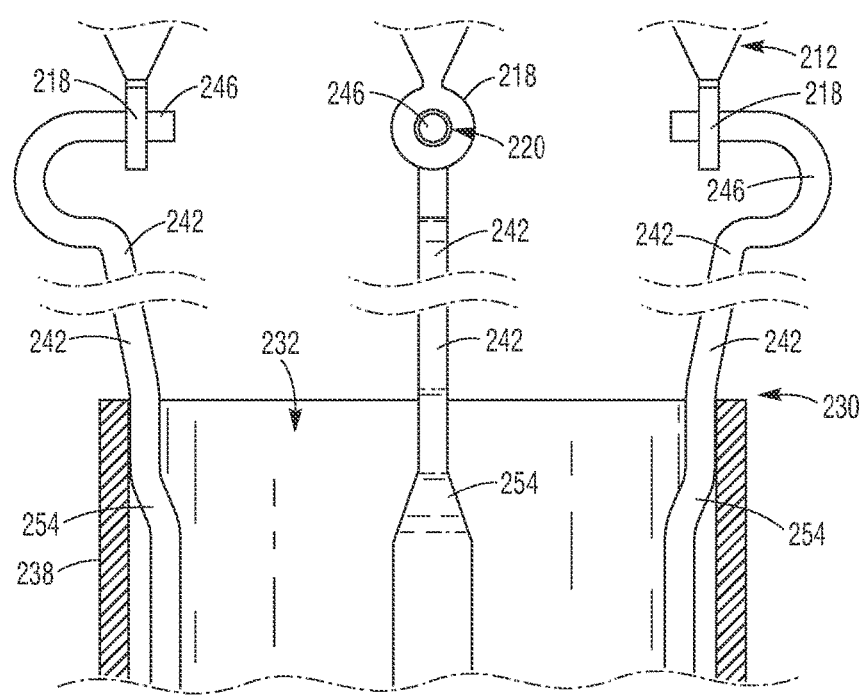

METHODS FOR CONTROLLED HEART VALVE DELIVERY

CROSS-REFERENCE TO RELATED APPLICATIONS

This application is a continuation of U.S. patent application Ser. No. 16/378,307, filed on Apr. 8, 2019 and issuing as U.S. Pat. No. 11,033,387 on Jun. 15, 2021, which is a continuation of U.S. patent application Ser. No. 15/351,823, filed on Nov. 15, 2016 and issued as U.S. Pat. No. 10,265,169 on Apr. 23, 2019, which claims the benefit of U.S. Provisional Application No. 62/258,973, filed on Nov. 23, 2015, each of the related applications is incorporated by reference herein in its entirety.

FIELD

The present disclosure relates to implantable, expandable prosthetic devices and to methods and delivery assemblies for such prosthetic devices.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Because of the drawbacks associated with conventional open-heart surgery, percutaneous and minimally-invasive surgical approaches are garnering intense attention. In one technique, a prosthetic device is configured to be implanted in a much less invasive procedure by way of catheterization. For example, collapsible transcatheter prosthetic heart valves can be crimped to a compressed state and percutaneously introduced in the compressed state on a catheter and expanded to a functional size at the desired position by balloon inflation or by utilization of a self-expanding frame or stent.

A challenge of implanting a prosthetic valve via a catheterization is control and positioning of the distal end of the delivery apparatus (i.e., the end of the apparatus that is advanced into a patient's heart) and prosthetic valve during the implantation procedure. An additional challenge includes variation in anatomy between patients, which can make some delivery apparatuses or methods unsuitable for patients with particular anatomy.

Thus, there is a continuing need for improved transcatheter prosthetic devices and delivery apparatuses for implanting such devices.

SUMMARY

Embodiments of improved prosthetic implant delivery assemblies are disclosed herein, as well as related methods and devices for such assemblies. In several embodiments, the disclosed assemblies are configured for delivering replacement heart valves into a heart of a patient.

In one representative embodiment, a prosthetic implant delivery assembly can comprise a prosthetic implant comprising an expandable stent portion having a longitudinal axis extending from a first end portion of the stent to a second end portion of the stent, and an elongate catheter having a longitudinal axis extending from a proximal end portion of the catheter to a distal end portion of the catheter and a plurality of arms extending axially from the distal end of the catheter, wherein the first end portion of the stent is releasably and pivotably coupled to at least one the arms of the catheter such that the stent can pivot about the at least one of the arms so that the longitudinal axis of the stent is tilted relative to the longitudinal axis of the catheter.

In some embodiments, the first end portion of the stent comprises a plurality of apices which are circumferentially-spaced apart relative to each other, each of the arms of the catheter comprises an aperture at a distal end of the arm, and the apices extend through respective apertures of the arms.

In some embodiments, the delivery assembly further comprises a plurality of elongate locking elements corresponding to the arms of the catheter, wherein each of the apices of the stent comprises a respective opening, and the locking elements are configured to extend through the openings of the apices of the stent, such that the locking elements releasably couple the arms of the catheter to the stent when the apices of the stent are inserted through the apertures of the arms. In some embodiments, at least one of the locking elements is axially moveable relative to another locking element. In some embodiments, a length of at least one of the locking elements is different than a length of another locking element.

In some embodiments, at least one of the apertures of the arms has a different length than another aperture of the arms. In some embodiments, the catheter further comprises a plurality of sleeves, and the sleeves are configured to be axially slidable relative to a respective aperture of the arms such that the sleeves can be used to alter an effective size of the aperture of the arm, wherein the effective size of the aperture is the portion of the aperture that is unobstructed by the sleeve. In some embodiments, at least one arms of the catheter is axially moveable relative to another arm. In some embodiments, a length of at least one arm of the catheter is different than a length of another arm.

In some embodiments, the delivery assembly is configured for implanting the prosthetic implant to a native aortic valve via a retrograde approach.

In some embodiments, the longitudinal axis of the stent can tilt up to 60 degrees relative to the longitudinal axis of the catheter. In some embodiments, the longitudinal axis of the stent can tilt from 0 degrees to 45 degrees relative to the longitudinal axis of the catheter.

In another representative embodiment, a prosthetic implant delivery assembly comprises a prosthetic implant comprising an expandable stent portion having a plurality of apices circumferentially spaced around a first end portion of the stent, wherein at least some of the apices comprise an aperture, and an elongate catheter comprising a plurality of radially expandable arms extending axially from a distal end of a shaft of the catheter, each arm having a hook portion which extends radially inwardly, wherein the hook portions of the arms releasably engage a respective aperture of the stent, and the arms of the catheter are configured such that the arms can expand radially relative to the catheter when the arms are exposed from within a sheath such that the hook portions disengage the apertures of the stent.

In some embodiments, the hook portions of the arms extend radially inwardly and are angled proximally.

In some embodiments, the expandable stent is a self-expandable stent. In some embodiments, the expandable arms of the catheter are self-expandable.

In some embodiments, the delivery assembly further comprises a shaft disposed radially within the catheter and an expanding element disposed on a distal end portion the shaft, wherein the expanding element is configured such that relative axial motion between the expanding member and the arms of the catheter in a first direction causes the arms to radially expand and relative axial motion between the expanding member and the arms of the catheter in a second direction allows the arms to radially compress. In some embodiments, the expanding element has a frusto-conical shape.

In some embodiments, the delivery assembly is configured such that relative rotational motion between the shaft and the expanding element causes relative axial motion between the expanding element and the arms of the catheter. In some embodiments, the delivery assembly is configured such that relative axial motion between the shaft and the arms causes relative axial motion between the expanding element and the arms of the catheter.

In some embodiments, the plurality of expandable arms comprises 2 to 15 arms.

The foregoing and other objects, features, and advantages of the invention will become more apparent from the following detailed description, which proceeds with reference to the accompanying figures.

BRIEF DESCRIPTION OF THE DRAWINGS

FIG. 17 is a perspective view of another embodiment of a prosthetic implant delivery assembly.

FIG. 18 is a detail view of the prosthetic implant delivery assembly of FIG. 17.

DETAILED DESCRIPTION

Figure 1:
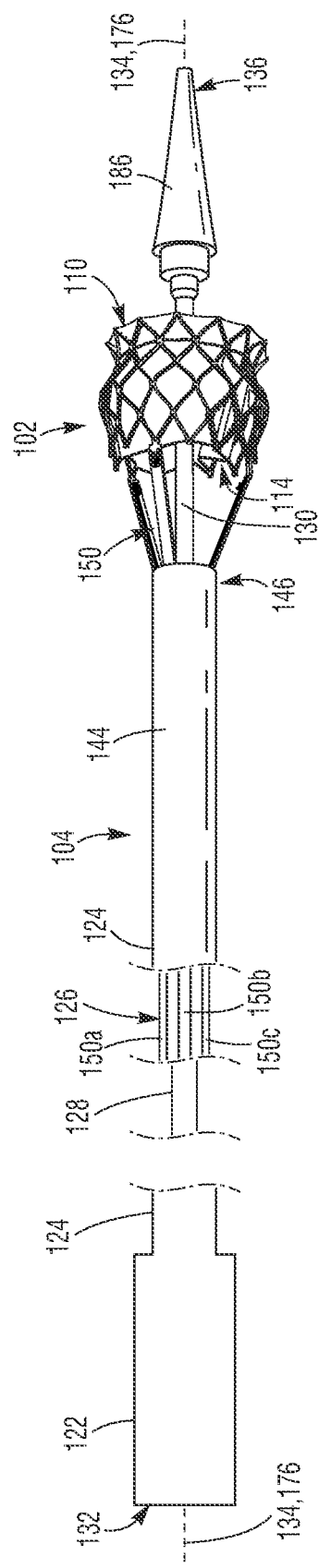
FIG. 1 is a perspective view of an embodiment of a prosthetic implant delivery assembly.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms "a," "an," and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C," or "A, B, and C."

As used herein, the term "coupled" generally means physically coupled or linked and does not exclude the presence of intermediate elements between the coupled items absent specific contrary language.

Described herein are examples of prosthetic implant delivery assemblies and components thereof which can improve a physician's ability to control the distal end of the delivery assembly during the implantation procedure and which can be used on patients with various anatomies.

For example, in some embodiments, a delivery assembly can allow a prosthetic valve to be tilted relative to a delivery apparatus so that the prosthetic valve can be deployed coaxially with a native annulus of a heart, even if the delivery apparatus is not coaxial with the native annulus of the heart. In some embodiments, for example, a delivery assembly can be used to recapture and/or reposition a prosthetic heart valve that has been deployed with a native annulus of a heart.

In some embodiments, a delivery assembly (e.g., the delivery assembly 100 and the delivery assembly 200) is adapted to deliver and implant a prosthetic heart valve in a native aortic annulus or valve of a heart using a retrograde approach (see, e.g., FIGS. 12-16), although in other embodiments it can be adapted to deliver and implant a prosthetic valve in the other native annuluses of the heart (e.g., the pulmonary, mitral, and tricuspid annuluses) and/or to be used with various other approaches (e.g., antegrade, transseptal, transventricular, transatrial, etc.).

A delivery assembly (e.g., the delivery assembly 100 and the delivery assembly 200) can also be adapted to deliver and implant a prosthetic valve in other tubular organs or passageways in the body. Further, in addition to prosthetic valves, a delivery assembly can be adapted to deliver and implant various other prosthetic devices such as stents and/or other prosthetic repair devices.

FIG. 1 shows an example of a prosthetic implant delivery assembly 100, according to one embodiment. The delivery assembly 100 can comprise two main components: a prosthetic heart valve 102 and a delivery apparatus 104. The prosthetic valve 102 can be releasably and pivotably coupled to the delivery apparatus 104, as further described below.

Figure 3:
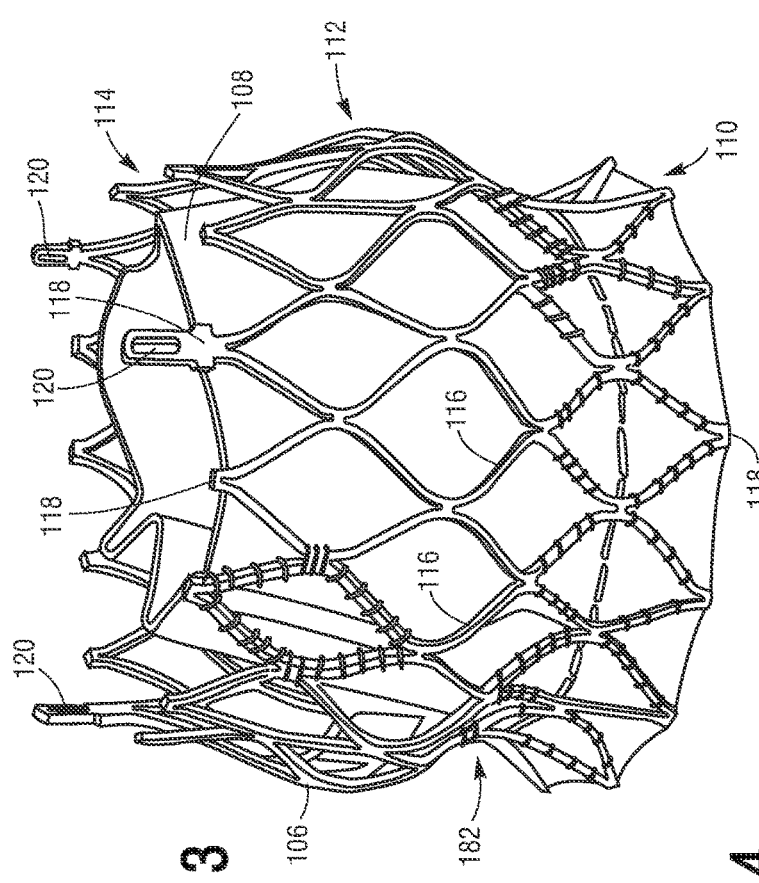
FIG. 3 is a perspective view of the prosthetic implant of the delivery assembly of FIG. 1.

Referring now to FIG. 3, the prosthetic valve 102 can comprise an annular stent or frame 106 and a valve structure 108 which is coupled to the frame 106. The prosthetic valve 102 can have in inflow end portion 110, and intermediate portion 112, and an outflow end portion 114.

The frame 106 can comprise a plurality of interconnected struts 116 arranged in a lattice-type pattern and forming a plurality of apices 118 at the inflow and outflow ends 110, 114 of the prosthetic valve 102. As shown, at least some of the apices 118 at the outflow end 114 of the prosthetic valve 102 can have a respective aperture or opening 120 formed therein (e.g., three in the illustrated embodiment). The openings 120 can, for example, be used to releasably and pivotably couple the prosthetic valve 102 to the delivery apparatus 104, as further explained below (see FIGS. 5A-5C).

The apices 118 having the openings 120 can be arranged in various ways relative to each other and relative to the other apices 118 at the outflow end 114 of the prosthetic valve 102. For example, the apices 118 having the openings 120 can be uniformly (e.g., symmetrically) distributed circumferentially around the outflow end 114 of the prosthetic valve 102 relative to the other apices 118 at the outflow end 114 of the prosthetic valve 102. The apices 118 with the openings 120 can be referred to as connecting arms, or connecting posts, and can be longer than the apices without the openings 120.

The frame 106 can be made of any of various suitable plastically-expandable materials (e.g., stainless steel, etc.) or self-expanding materials (e.g., nickel titanium alloy ("NiTi"), such as Nitinol) as known in the art. When constructed of a plastically-expandable material, the frame 106 (and thus the prosthetic valve 102) can be crimped to a radially collapsed configuration or state on a delivery catheter and then expanded inside a patient by an inflatable balloon or equivalent expansion mechanism to a functional state. When constructed of a self-expandable material, the frame 106 (and thus the prosthetic valve 102) can be crimped to a radially collapsed configuration (see, e.g., FIG. 3) and restrained in the collapsed configuration by insertion into a sheath or equivalent mechanism of a delivery catheter. Once inside the body, the prosthetic valve can be advanced from the delivery sheath, which allows the prosthetic valve to radially expand to its functional state (e.g., FIGS. 15-16).

Further details regarding the collapsible transcatheter prosthetic heart valves, including the manner in which the valve structure 108 can be coupled to the frame 106 of the prosthetic valve 102 can be found, for example, in U.S. Pat. Nos. 6,730,118, 7,393,360, 7,510,575, 7,993,394, and 8,652, 202, which are incorporated herein by reference in their entirety.

Referring again to FIG. 1, the delivery apparatus 104 can comprise a handle 122, an outer catheter 124, a release catheter 126, and a locking catheter 128. The handle 122 can be disposed adjacent to a proximal end portion 132 of the delivery apparatus 104. The outer catheter 124, the release catheter 126, and the locking catheter 128 can extend coaxially along a longitudinal axis 134 from the proximal end 132 of the delivery apparatus 104 toward an opposite, distal end portion 136 of the delivery apparatus 104. The release catheter 126 and the locking catheter 128 can be disposed radially within and extend axially through a lumen of the outer catheter 124. The locking catheter 128 can be disposed radially within and extend axially through a lumen 140 (see FIG. 6) of the release catheter 126.

The outer catheter 124, the release catheter 126, and the locking catheter 128 can each be independently moveable relative to each other. In some embodiments, the delivery apparatus 104 can be configured such that relative axial movement between two or more of the catheters 124, 126, 128 at the proximal end 132 of the delivery apparatus 104 can cause corresponding relative axial movement at or near the distal end 136 of the delivery apparatus 104. For example, the delivery apparatus 104 can be configured such that axially advancing a proximal end of the release catheter 126 in the distal direction while maintaining the axial position of the outer catheter 124, and the locking catheter 128 causes a distal end of the release catheter 126 to axially advance in the distal direction relative to the outer catheter 124 and the locking catheter 128.

In an alternative embodiment, the delivery apparatus 104 can be configured such that relative rotational movement between two or more of the catheters 124, 126, 128 at or near the proximal end of the delivery apparatus 104 can cause corresponding relative axial movement at or near the distal end 136 of the delivery apparatus 104. For example, the delivery apparatus 104 can be configured such that rotating the proximal end of the release catheter 126 in a first direction while preventing rotational movement of the outer catheter 124 and the locking catheter 128 causes the distal end of the release catheter 126 to rotate in the first direction relative to the outer catheter 124 and the locking catheter 128.

The outer catheter 124 can comprise a sheath portion 144 disposed at a distal end 146 of the outer catheter 124. The sheath 144 can be used to retain the prosthetic valve 104 in a radially compressed state during delivery of the prosthetic valve 102 through a patient's body, as further described below.

Figure 6:
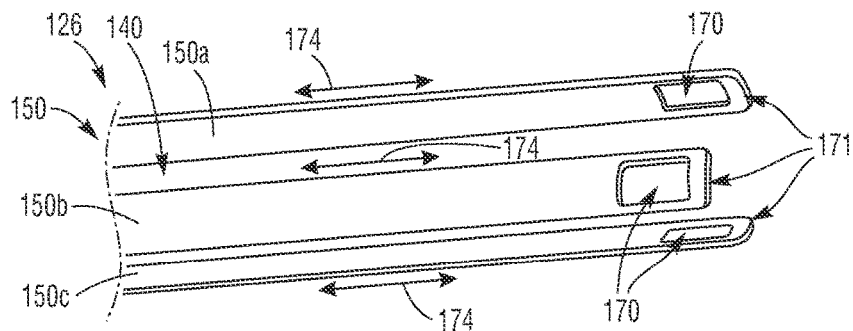
FIG. 6 is a perspective view of an embodiment of a release catheter of the delivery assembly of FIG. 1.

Referring now to FIG. 6, the release catheter 126 can comprise a shaft portion (not shown) and a plurality of tines or arms 150a, 150b, 150c (collectively referred to herein as "the arms 150"). The arms 150 can extend axially from a distal end of the shaft and can be spaced apart circumferentially relative to each other. Although the illustrated embodiment shows three arms (e.g., the arms 150a, 150b, 150c) other embodiments can, for example, have less or more arms (e.g., two, four, five, or six arms). The arms 150 of the release catheter 126 can each have a respective aperture or window 170 disposed near the distal ends 171 of the arms 150.

Figure 4:
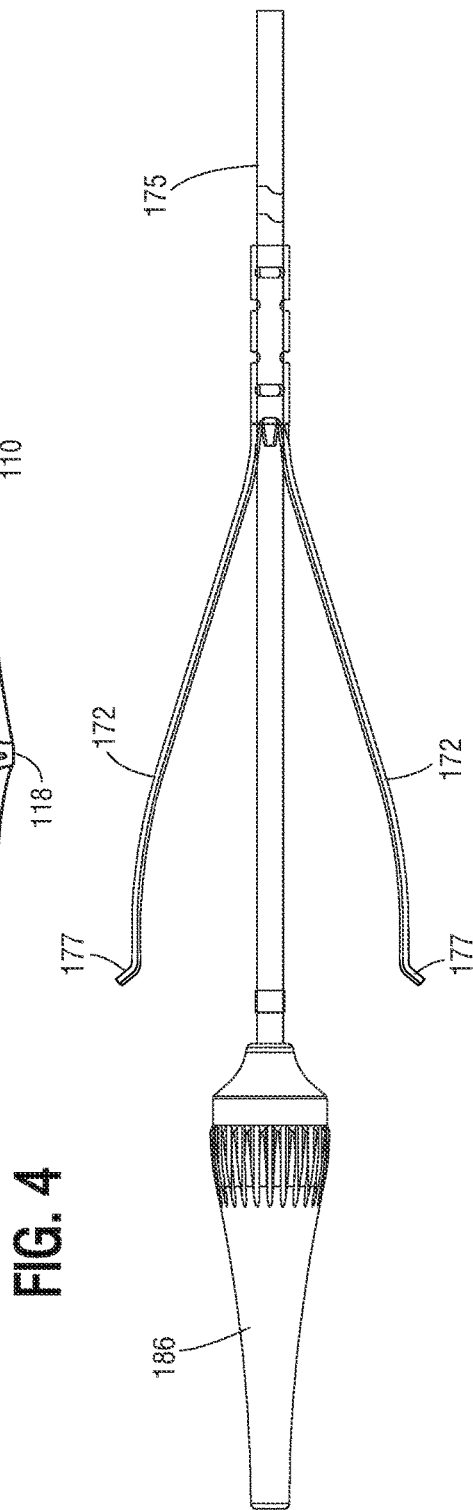
FIG. 4 is a side view of a locking catheter of the delivery assembly of FIG. 1.

Referring now to FIG. 4, the locking catheter 128 can, for example, comprise a shaft 175 and locking elements or arms 172a, 172b, and 172c (collectively referred to herein as "the arms 172") mounted at a location along the distal end portion of the shaft 175. The arms 172 can be spaced apart circumferentially relative to each other. Although the illustrated embodiment shows three arms (e.g., the arms 172a, 172b, 172c) (one locking arm 172 for each release arm 150), other embodiments can, for example, have less or more arms (e.g., two, four, five, or six arms). The arms 172 of the locking catheter 128 can each have a bent or flared tip portion 177 which extends radially outward relative to the rest of the arm 172, as best shown in FIG. 4. The flared tips portions 177 can facilitate improved interlocking between the apices 118 of the prosthetic valve 102 and the arms 172 of the locking catheter 128, as further described below.

Figure 5A:
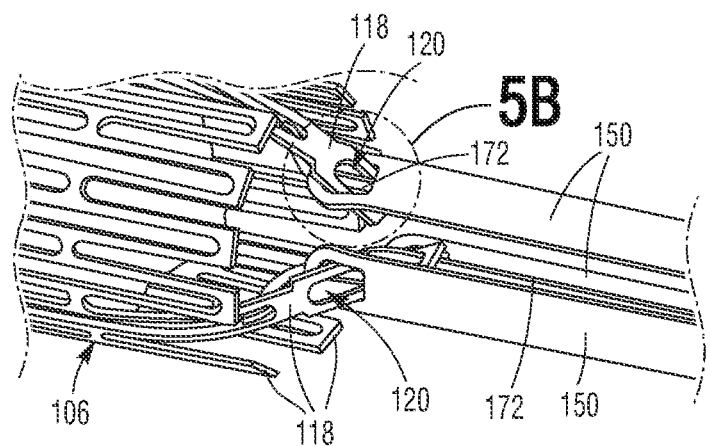
FIG. 5A is a perspective view of the delivery assembly of FIG. 1 with the prosthetic implant in a compressed configuration.
Figure 5B:
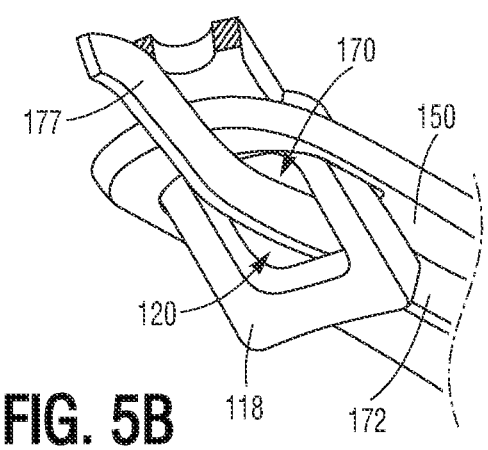
FIGS. 5B-5C are enlarged perspective views of the delivery assembly of FIG. 1 which show an area 5B, as indicated in FIG. 5A.
Figure 5C:
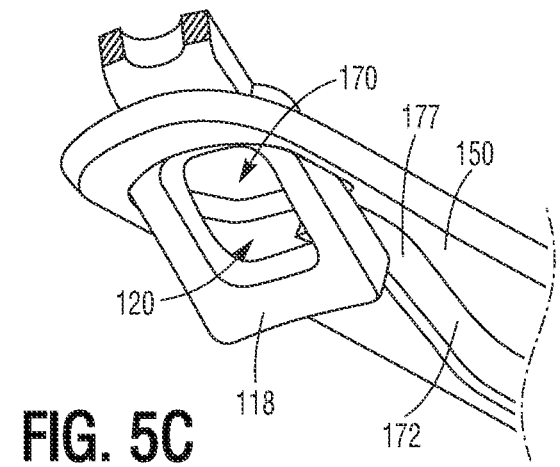

The prosthetic valve 102 can be releasably and pivotably coupled to the release catheter 126, for example, by inserting the apices 118 of the prosthetic valve 102 with the openings 120 into respective windows 170 of the release catheter 126, as best shown in FIGS. 5A-5C. The apices 118 of the prosthetic valve 102 can then be releasably secured within the windows 170 of the release catheter 126 by inserting a respective locking element or arm 172 of the locking catheter 128 radially between the apices 118 of the prosthetic valve 102 and the arms 150 of the release catheter 126 (see FIG. 5A) and advancing the arms 172 of the locking catheter 128 axially relative to the prosthetic valve 102 and the release catheter 126 such that the arms 172 of the locking catheter 128 extend through the openings 120 of the prosthetic valve 102, as best shown in FIG. 5B.

Coupling the prosthetic valve 102 to the release catheter 126 in this manner allows the prosthetic valve 102 to be released from the release catheter 126 by retracting the arms 172 proximally relative to the release catheter 126 so that the arms 172 of the locking catheter withdraw from the openings 120 of the prosthetic valve 102, which allows the apices 118 of the prosthetic valve 102 to slide out of the windows 170 of the release catheter 126. Coupling the prosthetic valve 102 to the release catheter 126 in this manner also allows the prosthetic valve 102 to tilt or pivot relative the release catheter 126 because the prosthetic valve 102 can pivot about the apices 118 of the prosthetic valve within the windows 170 of the release catheter 126, as further described below.

In some embodiments, the arms 150 of the release catheter 126 can be independently axially moveable, relative to each other. For example, as shown in FIG. 6, the arms 150a, 150b, and 150c can each be independently axially moveable relative to each other (e.g., in the direction shown by arrows 174). In particular embodiments, each arm 150 can extend axially into the handle 122 of the delivery apparatus 104 and each arm can be manipulated by a respective actuator (not shown) on or adjacent to the handle 122. In some embodiments, the proximal end portions of the arms 150 can be supported on or coupled to a common shaft that allows independent axial movement of each arm.

Figure 2:
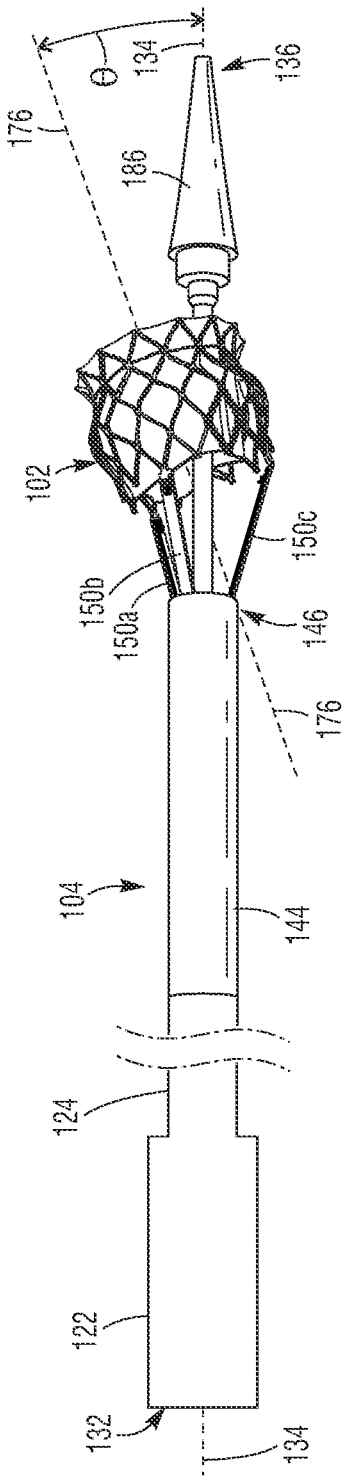
FIG. 2 is a perspective view of the delivery assembly of FIG. 1 with the prosthetic implant in a tilted configuration.

Configuring the release catheter 126 in this manner allows the release catheter 126 to be used to pivot or tilt the prosthetic valve 102 relative to the release catheter 126 and thus the delivery apparatus 104. For example, as shown in FIG. 1, a longitudinal axis 176 of the prosthetic valve 102 can be aligned with the longitudinal axis 134 of the delivery apparatus 104 when the arms 150 of the release catheter 150 are in the same axial position relative to each other. The prosthetic valve 102 can be tilted, for example, by moving the arms 150 of the release catheter 126 axially relative to each other such that the arms 150 are not all in the same axial position relative to each other, as shown in FIG. 2. This causes the longitudinal axis 176 of the prosthetic valve 102 to tilt, relative to the longitudinal axis 134 of the delivery apparatus 104, toward the arm 150 that retracted the farthest (e.g., the arm 150a in FIG. 2) such that the axes 134, 176 are offset relative to each other by an angle θ.

In some embodiments, for example, the prosthetic valve 102 can be tilted relative to the delivery apparatus 104 such that the angle θ is up to 60 degrees (e.g., from 0 to 60 degrees). In other embodiments, for example, the prosthetic valve 102 can be tilted relative to the delivery apparatus such that the angle θ is from 0 to 45 degrees, from 0 to 30 degrees, or from 0 to 15 degrees.

Figure 16:
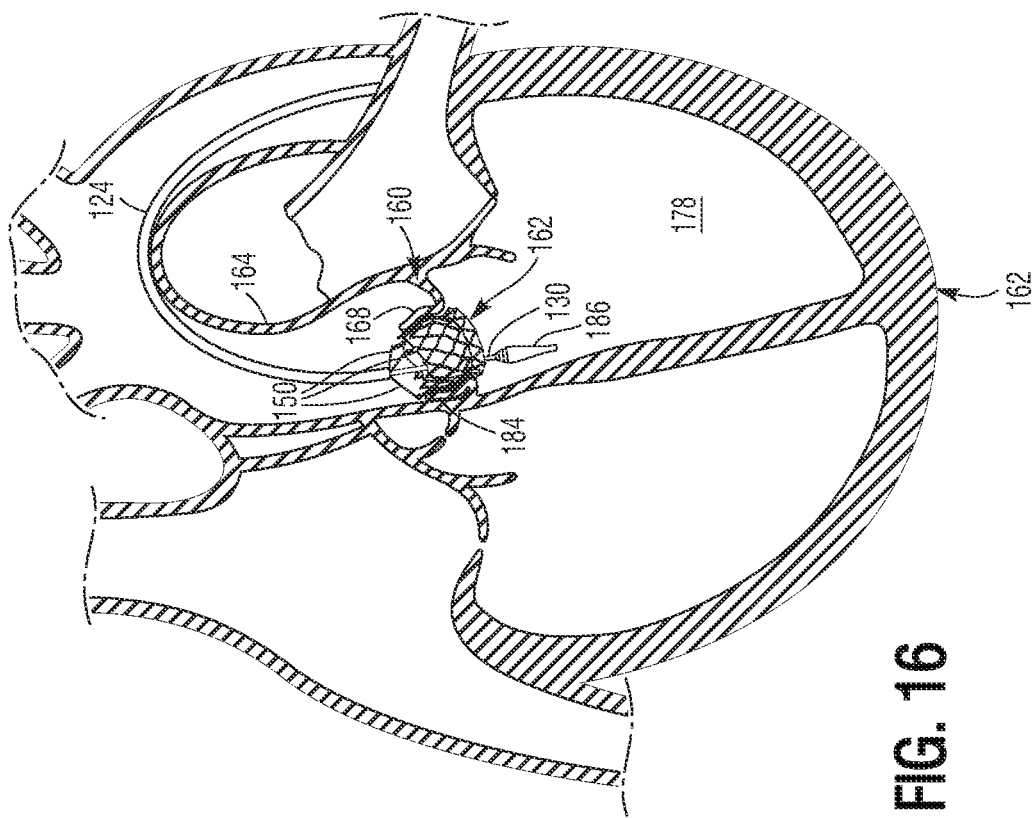
Figure 15:
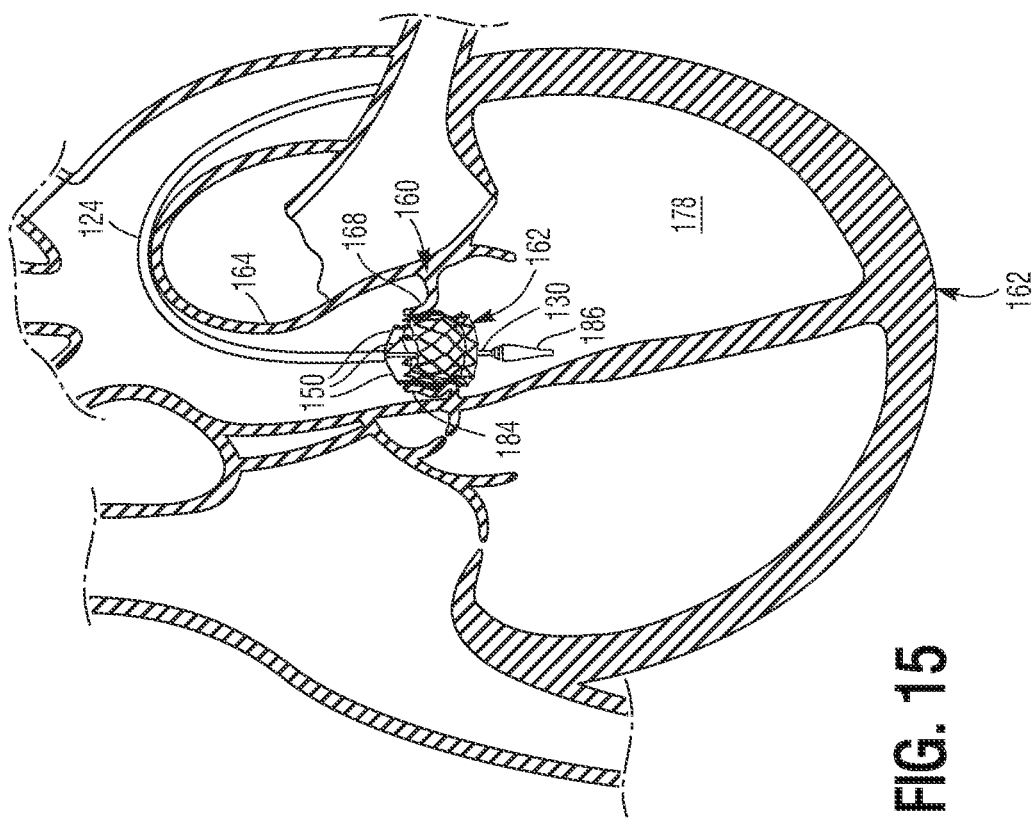

In this manner, the delivery apparatus 104 can allow a physician to actively manipulate a prosthetic valve in order to desirably position the prosthetic valve at an implantation site. For example, FIG. 15 shows one portion of the prosthetic valve 102 (e.g., the left side of the prosthetic valve 102 in FIG. 15) desirably positioned within the native annulus 160 and another portion of the prosthetic valve 102 (e.g., the right side of the prosthetic valve 102 in FIG. 15) undesirably positioned within the native annulus 160 (e.g., too low in the annulus in FIG. 15). To align the prosthetic valve 102 with the native annulus 160, the physician can proximally retract (e.g., pull back) one or more of the arms 150 (e.g. the rightmost arm(s) 150 in FIG. 15) of the delivery apparatus 104 while maintaining the positioning of one or more of the arms 150 (e.g., the leftmost arm(s) 150 in FIG. 15) of the delivery apparatus 104 such that the prosthetic valve tilts (e.g., the right side moves upwardly) relative to the inner catheter 130, as shown in FIG. 16.

Additionally, the delivery apparatus 104 can allow a prosthetic valve to self-align relative to a native annulus by allowing the prosthetic valve to tilt relative to the delivery apparatus 104. For example, as best shown in FIG. 1, the frame 106 of the prosthetic valve 102 can be configured to have a radially-tapered "waist" portion 182 which is disposed between the inflow end 110 and the intermediate portion 112 of the prosthetic valve 102. The waist portion 182 can have a relatively smaller radius than the inflow end 110 and the intermediate portion 112 of the prosthetic valve 102. As a result, the waist portion 182 of the prosthetic valve 102 tends to align itself with the native annulus 160 when the prosthetic valve 102 radially-expands to its functional state and begins to oppose the native leaflets (e.g., the leaflets 168, 184) and the native annulus 160, as best shown, for example, in FIG. 16. Accordingly, the prosthetic valve 102 can remain coaxial with the delivery apparatus 104, and thus the native annulus 160, if the delivery apparatus 104 is coaxial with the native annulus 160 when the prosthetic valve 102 is deployed; however, the prosthetic valve 102 can move proximally and/or tilt so that the prosthetic valve 102 is relatively more coaxial with the native annulus 160 if the delivery apparatus 104 is not coaxial with the native annulus 160 when the prosthetic valve 102 is deployed (see, e.g., FIG. 16).

Although in the illustrated embodiment the outflow end (the proximal end) of the prosthetic valve is releasably coupled to the delivery apparatus, in other embodiments, the inflow end (the distal end) of the prosthetic valve can be releasably coupled to the delivery apparatus. Also, the orientation of the prosthetic valve can be inverted relative to the delivery apparatus such that the inflow end of the prosthetic valve is the proximal end and the outflow end of the prosthetic valve is the distal end. This can, for example, allow the delivery assembly to be configured for various implantation locations (e.g., the native aortic, pulmonary, mitral, and tricuspid annuluses) and/or for various delivery approaches (e.g., antegrade, transseptal, transventricular, transatrial).

Figure 7:
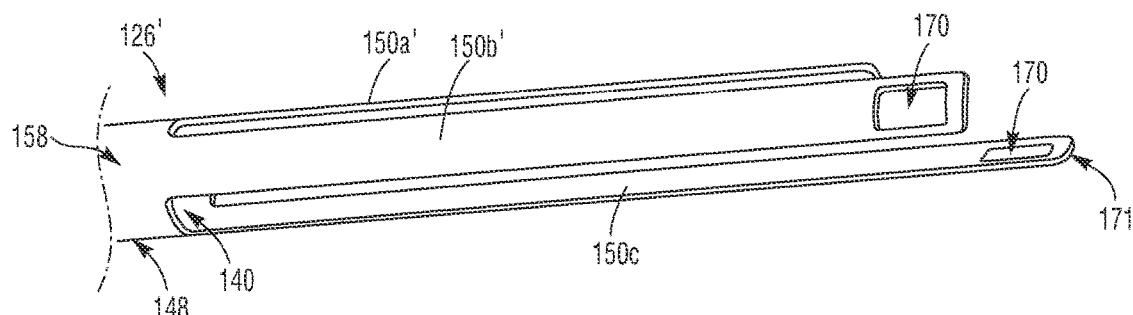
FIG. 7 is a perspective view of another embodiment of a release catheter of the delivery assembly of FIG. 1.

In lieu of or in addition to axially moveable release catheter arms, in some embodiments, a release catheter 126' can have arms having different axial lengths relative to each other. For example, as shown in FIG. 7, an arm 150b' is axially longer than an arm 150a', and an arm 150c' is axially longer than the arms 150a' and 150b'. Configuring the arms 150 of the release catheter 126' in this manner causes the prosthetic valve 102 to tilt or pivot relative delivery apparatus 104 toward the shortest arm 150 (e.g., the arm 150a' in FIG. 7) at the angle θ when the sheath 144 of the delivery apparatus 104 is retracted relative to the prosthetic valve 102 and the prosthetic valve 102 expands to its functional configuration (see, e.g., FIG. 2).

Figure 8:
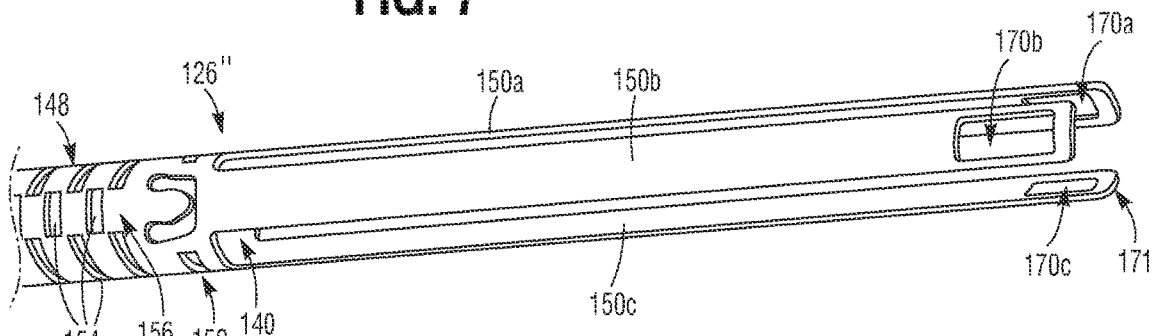
FIG. 8 is a perspective view of another embodiment of a release catheter of the delivery assembly of FIG. 1.

In lieu of or in addition to any of the previously described examples, in some embodiments, a release catheter 126" can have release arms 150a, 150b, 150c having windows that are sized differently relative to each other, as shown in FIG. 8. For example, the release catheter 126" comprises a window 170b which is axially longer than windows 170a, 170c. Configuring the windows of the release catheter 126" in this manner allows the prosthetic valve 102 to tilt or shift proximally relative delivery apparatus 104 toward the longest window (e.g., the window 170b in FIG. 8) at the angle θ when the sheath 144 of the delivery apparatus 104 is retracted relative to the prosthetic valve 102 and the prosthetic valve 102 expands to its expanded configuration (see, e.g., FIG. 2).

The release catheter 126" can also have a plurality of circumferential openings or slots 154 which extend axially along a shaft portion 148 of the release catheter 126". The slots 154 can be configured so as to allow the release catheter 126" to bend relatively more easily in the direction of the slots 154. As such, the release catheter 126" can be formed with the slots 154 formed in a first circumferential side portion 156 of the shaft 148; whereas, a second circumferential side portion 158 (FIG. 7) of the shaft 148 can be formed without slots. This configuration allows the release catheter 126" to bend relatively more easily toward the first side 156 of the shaft 148 than toward the second side 158 of the shaft 148.

The release catheter 126" can also be configured such that one of the arms of the release catheter 126" can be axially aligned with the side of the shaft 148 that has the slots 154. For example, as shown in FIG. 8, the arm 150b is axially aligned with the first side 156 of the shaft 148 which has the slots 154. Aligning one of the arms 150 (e.g., the arms 150b) with the relatively more flexible side (e.g., the first side 156) of the shaft 148 advantageously allows a physician to predetermine the orientation of the arms 150 of the release catheter 126" relative to the patient's native anatomy when the delivery assembly 100 is advanced into the patient's body.

For example, when using the delivery assembly 100 to deliver the prosthetic valve 104 to a native aortic annulus 160 of a heart 162 using a retrograde approach (e.g., as shown in FIG. 15), the release catheter 126" can orient itself such that the slots 154 (FIG. 8) are adjacent to an inside curved portion 164 of an aortic arch 166 because the release catheter 126" tends to flex toward the first side 156 due to the slots 154 in the shaft 148. Thus, because the arm 150b is aligned with the first side 156 of release catheter 126", the arm 150b desirably is directed toward the inside curve 164 of the aortic arch 166, adjacent to a native left coronary leaflet or cusp 168 of the native aortic valve.

Figure 9:
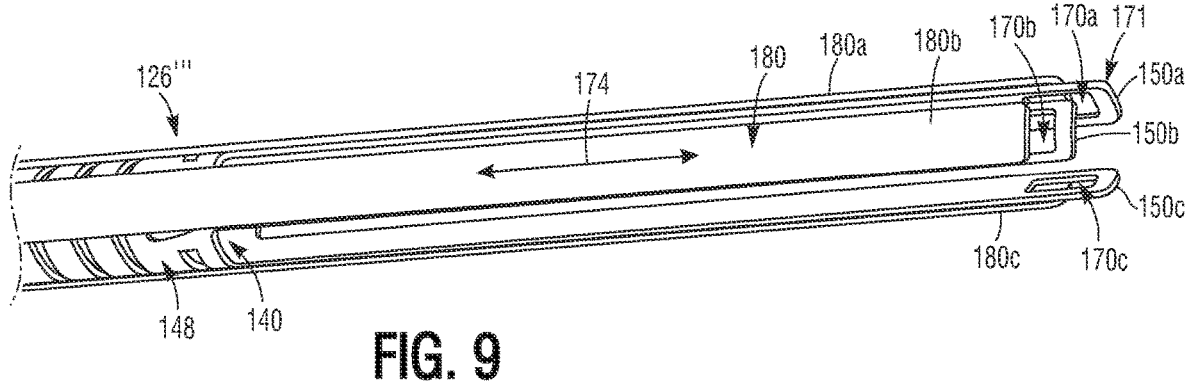
FIG. 9 is a perspective view of another embodiment of a release catheter of the delivery assembly of FIG. 1.

In lieu of or in addition to the any of the previously described examples, in some embodiments, a release catheter 126''' can have one or more sleeves, each of which is slidably coupled to a respective arm 150 of the release catheter 126'''. For example, as shown in FIG. 9, the release catheter 126''' has three sleeves 180a, 180b, 180c (collectively referred to herein as "the sleeves 180") which are slidably coupled to the arms 150a, 150b, 150c, respectively. The sleeves 180 can be independently axially slidable both relative to the arms 150 and to each other. As such, the sleeves 180 can be used to effectively alter the length of windows by axially sliding the sleeves 180 relative to a respective window (e.g., in the direction shown by arrow 174).

For example, sliding the sleeve 180b of the release catheter 126''' proximally relative to the window 170b of the release catheter 126''' (while maintaining the positioning of the sleeves 180a, 180c relative to the respective windows 170a, 170c) effectively lengthens or extends the window 170b. As such, the window 170b can be effectively longer than the windows 170a, 170c, which allows the prosthetic valve 102 to move and/or tilt relative delivery apparatus 104 (e.g., at the angle θ) toward the window 170b of the release catheter 126''' when the sheath 144 of the delivery apparatus 104 is retracted relative to the prosthetic valve 102 and the prosthetic valve 102 expands to its functional configuration.

Figure 10:
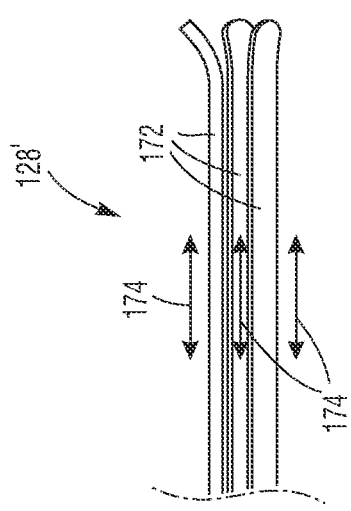
FIG. 10 is a perspective view of another embodiment of a locking catheter of the delivery assembly of FIG. 1.

In lieu of or in addition to any of the previously described examples, in some embodiments, a locking catheter 128' have locking arms that can be independently axially moveable, relative to each other. For example, as shown in FIG. 10, the locking catheter 128' can comprise locking arms 172 that can each be independently moved axially (e.g., in the direction shown by arrows 174). In particular embodiments, each locking arm 172 can extend axially into the handle 122 and each arm can be manipulated by a respective actuator (not shown) on or adjacent the handle. In some embodiments, the proximal end portions of the arms 172 can be supported on or coupled to a common shaft that allows independent movement of each arm.

Configuring the locking catheter 128' in this manner allows the apices 118 of the prosthetic valve 102 to be released from the delivery apparatus 104 simultaneously by retracting the arms 172 of the locking catheter 128' proximally relative to the release catheter 126 at the same time or sequentially by retracting the arms 172 of the locking catheter 128' proximally relative to the release catheter 126 at different rates and/or different times relative to each other.

Releasing the apices 118 of the prosthetic valve 102 from the delivery apparatus 104 sequentially can, for example, allow the prosthetic valve 102 to tilt relative to the delivery apparatus 104, thereby allowing the prosthetic valve 102 to self-align with the native annulus 160, as described above. In addition, releasing one or more of the apices 118 of the prosthetic valve 102 can allow the physician to actively manipulate the positioning of the prosthetic valve 102 relative to the native annulus 160 by moving the release catheter 126 and/or the arms 150 of the release catheter 126 that remain attached to the prosthetic value 102 axially. This axial movement can cause the prosthetic valve 102 to move and/or tilt (e.g., at the angle θ) relative to the delivery apparatus 104 and thus relative to the native annulus 160.

Figure 11:
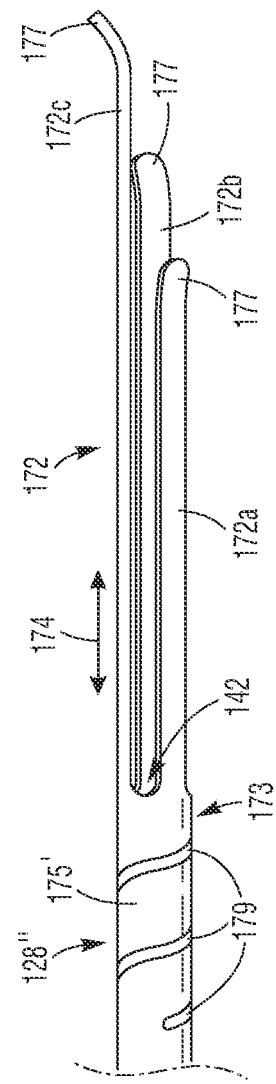
FIG. 11 is a perspective view of another embodiment of a locking catheter of the delivery assembly of FIG. 1.

In some embodiments, a locking catheter 128" can have locking arms of different lengths. This can be in lieu of or in addition to the features of any of the previously described examples. For example, as shown in FIG. 11, the locking catheter 128" can comprise an arm 172b longer than an arm 172a, and an arm 172c longer than the arms 172a and 172b. Configuring the arms 172 of the locking catheter 128" in this manner allows the apices 118 of the prosthetic valve 102 to be released from the delivery apparatus 104 sequentially. This can be accomplished by retracting the locking catheter 128" proximally relative to the release catheter 126 such that the arms retract proximally from the openings 120 in the apices 118 of the prosthetic valve 102. As the locking catheter 128 retracts proximally relative to the release catheter 126, the apex 118 of the prosthetic valve 102 that corresponds to the arm 172a (i.e., the shortest arm) releases from the delivery apparatus 104 while the other arms 172b, 172c remain coupled to respective apices 118 of the prosthetic valve 102.

Referring to FIG. 11, a locking catheter 128" can comprise arms 172 extending from a distal end of a main shaft 175'. In this embodiment, the delivery apparatus 104 can include a separate shaft that extends co-axially through the shaft 175', with a nose cone 186 being mounted on the separate shaft. The main shaft 175' of the locking catheter 128" can have a plurality of circumferential slots 179 formed therein. The slots 179 can be use as ports, e.g., for an adhesive that is applied the delivery apparatus 104 during assembly. The slots 179 and/or additional slots (not shown) can be configured to allow the locking catheter 128" to bend more easily toward the first side of the main shaft 175' than towards a second side of the shaft 175' without slots formed therein (e.g., similar to the slots 154 formed in the shaft 148 of the release catheter 126").

The locking catheter 128" can be configured so that the slots 179 circumferentially align with the slots 154 of the release catheter 126" when the locking catheter 128" is inserted into and advanced axially through the lumen 140 of the release catheter 126. As such, the slots 154, 179 of the respective catheters 126, 128 can work together to allow the delivery apparatus 104 to bend more easily toward the side of the delivery apparatus 104 on which the slots 154, 179 are disposed.

It should be noted that the release catheters (e.g., release catheter 126") and the locking catheter (e.g., locking catheter 128") can, for example, be formed by laser-cutting respective alloy tubes. The alloy tubes can be formed from various suitable materials including stainless steel, Nitinol, and cobalt chromium.

Releasing one or more of the apices 118 of the prosthetic valve while the other apices 118 remain attached allows the prosthetic valve 102 to self-align with the native annulus (as described above) and/or allows the physician to manipulate the prosthetic valve 102 by axially moving the release catheter 126 which, in turn, causes the prosthetic valve 102 move and/or tilt (e.g., at the angle θ) so that the prosthetic valve 102 better aligns with the native annulus 160.

In this manner, the delivery assembly 100 can, for example, be oriented within the native aortic annulus 160 such that when the prosthetic valve 102 is expanded to its functional state the arm 172a of the locking catheter 128" is disposed adjacent to a non-coronary cusp (not shown) and the arms 172b, 172c are respectively disposed adjacent to a right coronary cusp 184 and the left coronary cusp 168 (see FIG. 15). The prosthetic valve 102 can then be aligned with the native aortic annulus 160 by retracting the locking catheter 128 proximally relative to the release catheter 126 so that the apex 118 of the prosthetic valve 102 that corresponds to the arm 172a of the locking catheter 128 is released from the delivery apparatus 104. The prosthetic valve 102 can then move from a non-aligned and/or non-coaxial positioning (see, e.g., FIG. 15) to a relatively more aligned and/or coaxial positioning (see, e.g., FIG. 16) by self-aligning relative to the native annulus 160 and/or by the physician axially moving the release catheter 126 which causes the prosthetic valve 102 to move and/or tilt relative to the delivery apparatus 104 so that the prosthetic valve 102 better aligns with the native annulus 160.

Configuring a delivery assembly so that a prosthetic valve can move and/or tilt relative to a delivery apparatus, for example as described above, can advantageously allow the prosthetic valve to be positioned coaxially or at least more coaxially within a native annulus of a heart in the event that the delivery apparatus cannot achieve the desired coaxiality relative to the native annulus.

Figure 12:
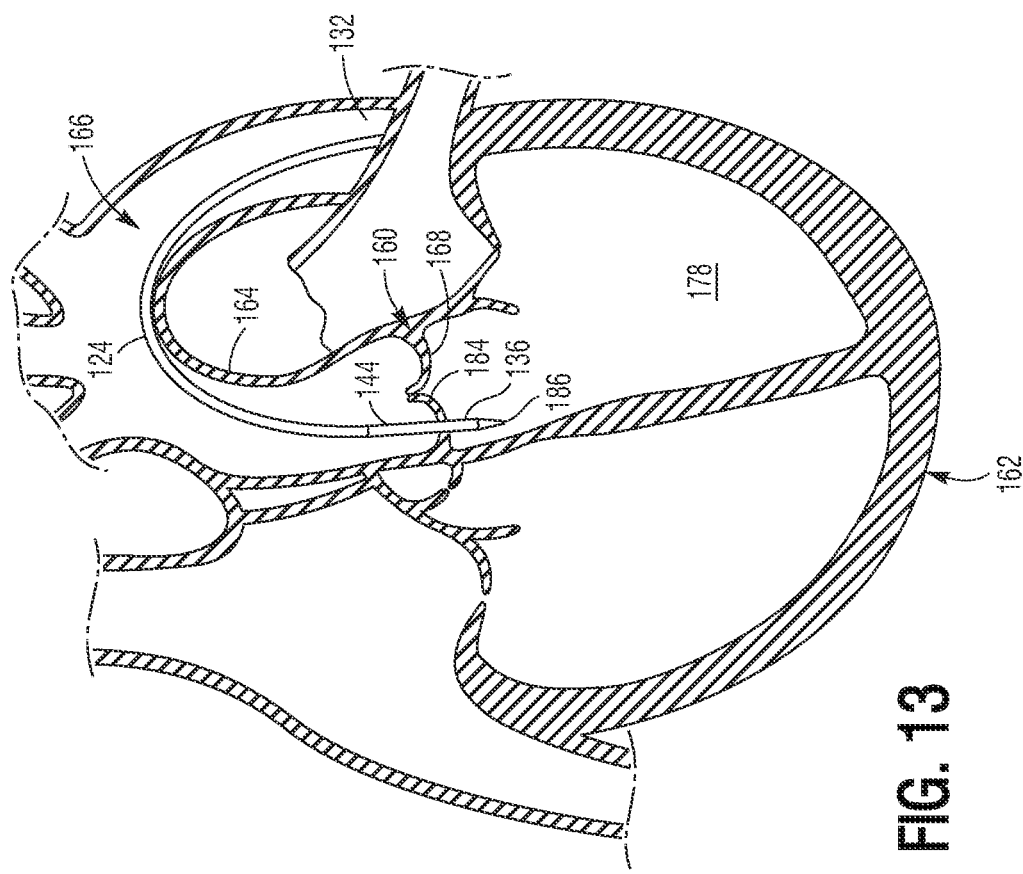
FIGS. 12-16 are perspective views of the delivery assembly of FIG. 1 being used to deliver a prosthetic implant into a patient's heart, shown in partial cross-section.
Figure 13:
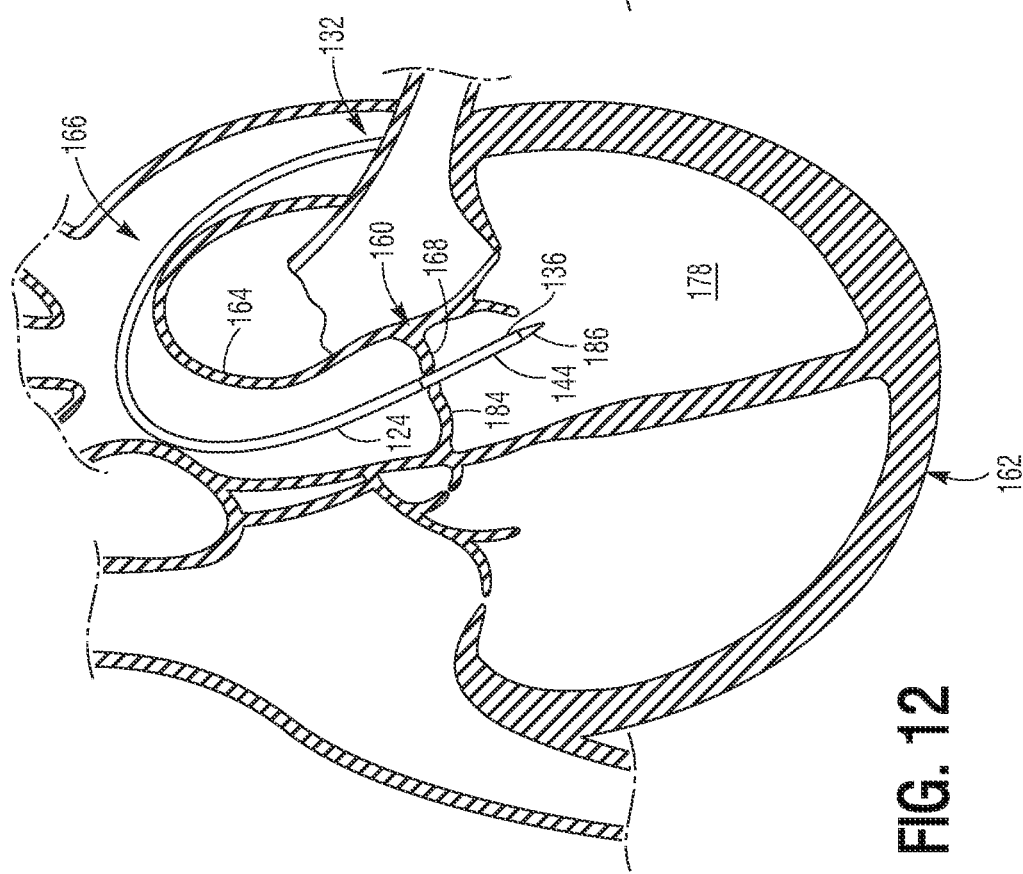

For example, FIGS. 12-16 show an example of a prosthetic valve implantation procedure using the delivery assembly 100. FIG. 12 shows the delivery assembly 100 inserted into a patient's vasculature and the distal end 136 of the delivery apparatus 104 and the prosthetic valve 102 (contained within the sheath 144 of the delivery apparatus 104 in the compressed configuration) advanced to the native aortic valve annulus 160 of the heart 162 using a retrograde approach. As shown in FIG. 12, the delivery apparatus 104 is approximately coaxial with the native aortic annulus 160, but the distal end 136 of the delivery apparatus 104 extends too deep into the left ventricle 178 relative to the native aortic annulus 160. As such, the prosthetic valve 102 would be improperly positioned relative to the native annulus 160 of the heart 162 if the prosthetic valve 102 was deployed from within the sheath 144 of the delivery apparatus 104. As shown in FIG. 13, the distal end 136 of the delivery apparatus 104 is better positioned relative to the native aortic annulus 160 and left ventricle 178 than the positioning shown in FIG. 12, but the distal end 136 of the delivery apparatus 104 and thus the prosthetic valve 102 would not be coaxial with the native annulus if the prosthetic valve 102 was deployed from within the sheath 144 of the delivery apparatus 104.

The inability to simultaneously achieve sufficient coaxiality (FIG. 12) and proper positioning relative to the native annulus (FIG. 13) can be caused by the relatively stiff distal end portion of a delivery assembly which prevents a distal end portion of the delivery apparatus from sufficiently bending so as to be coaxial with the native annulus. The distal end can be relatively stiff compared to other portions of the delivery assembly because of the concentration of material disposed at this portion of the delivery assembly, such as a compressed prosthetic valve and a relatively rigid delivery sheath.

This problem can be also be affected by the size of a prosthetic valve in a delivery assembly. For example, a larger prosthetic valve can increase the portion of the delivery assembly that is relatively stiff. For example, a prosthetic valve having a 29-mm diameter can result in a relatively stiff section of about 73 mm, a prosthetic valve having a 26-mm diameter can result in a relatively stiff section of about 67 mm, and a prosthetic valve having a 23-mm diameter can result in a relatively stiff section of about 62 mm (the relatively stiff section being measured from a distal end portion of the sheath toward the proximal end of the delivery apparatus.

In addition, this problem can be compounded by the length of a patient's ascending aorta (e.g., the distance from the aortic arch to the native aortic annulus). For example, a relatively short native ascending aorta provides relatively less room for the delivery apparatus to achieve coaxial alignment before the distal end of the delivery apparatus is disposed too deep into the left ventricle (see, e.g., FIG. 12).

Figure 14:
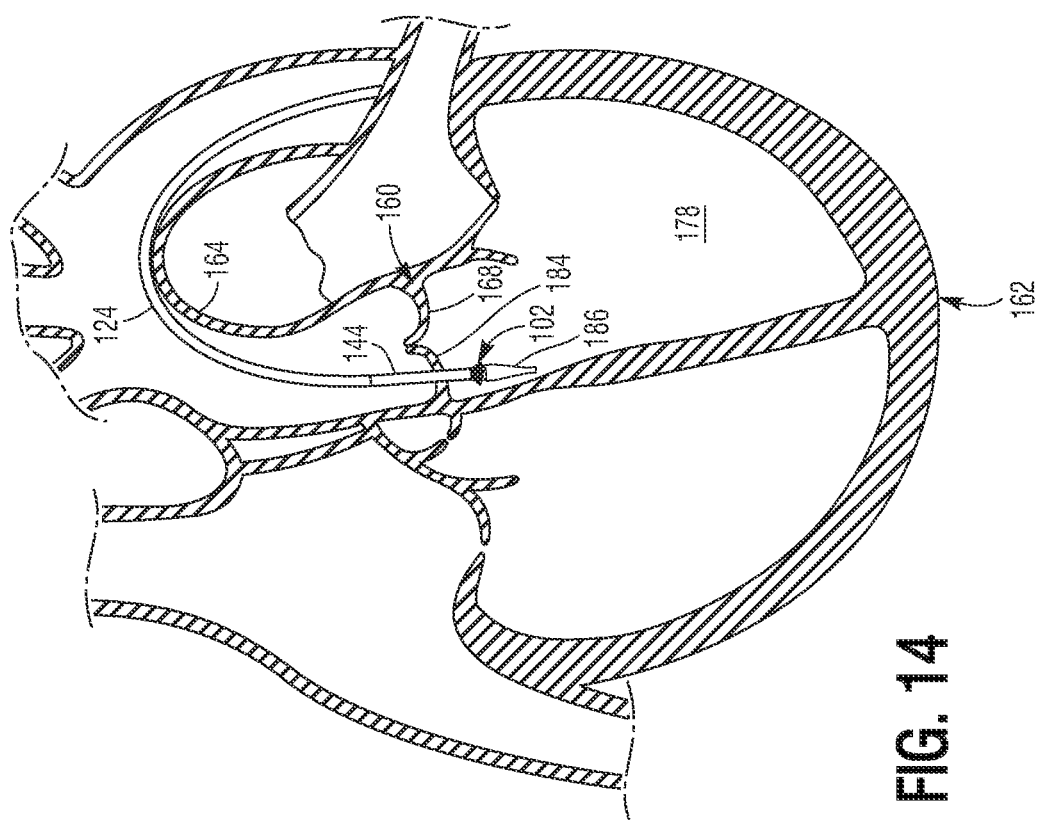

Referring now to FIG. 14, the prosthetic valve 102 can be deployed by retracting the outer catheter 124 proximally relative to the release catheter 126, which exposes the prosthetic valve 102 from within the sheath 144. When the prosthetic valve 102 is fully exposed from the sheath 144, the prosthetic valve 102 can radially self-expand to its functional state, as shown in FIG. 15. Alternatively, although not shown, the prosthetic valve 102 can be expanded to its functional state by inflating a balloon portion of the delivery apparatus 104 on which the prosthetic valve 102 is crimped if the frame 106 is formed from a plastically-expandable material.

If the prosthetic valve 102 is not coaxial relative to the native aortic annulus 160, for example as shown in FIG. 15, then the delivery apparatus 104 can be used to move and/or tilt the prosthetic valve 102 relative to the delivery apparatus 104, which can improve the coaxiality and/or the positioning of the prosthetic valve 102 relative to the native aortic annulus 160, for example as shown in FIG. 16. This can be accomplished by using any of the examples and/or techniques described above, including moving the arms 150 and/or sleeves 180 of the release catheter 126, moving the arms 172 of the locking catheter 128, etc.

Once the prosthetic valve 102 is desirably positioned within the native annulus 160, the prosthetic valve can be secured within the native annulus and released from the delivery apparatus 104. This can be accomplished by retracting the locking catheter proximally such that all of the arms 172 of the locking catheter 128 retract from the openings 120 in the frame 106 of the prosthetic valve 102, thereby releasing the apices 118 of the frame 106 from the windows 170 of the release catheter 126, and thus releasing the prosthetic valve 102 from the delivery apparatus 104.

The release catheter 126 and the locking catheter 128 can then be retracted proximally, such that the release and locking catheters 126, 128 are disposed in the outer catheter 124 and the nose cone 186 of the inner catheter 130 is adjacent to the sheath 144 of the outer catheter 124. The delivery apparatus 104 can then be removed from the patient's body by retracting the delivery apparatus 104 proximally.

In another embodiment, the delivery apparatus 104 can include a rotatable torque shaft that extends coaxially through the release catheter 126 and a sheath that is mounted on the distal end of the torque shaft. The sheath is operatively coupled to the torque shaft such that rotation of the torque shaft is effective to retract or advance the sheath relative to the implant. Further details of the delivery apparatus are disclosed in U.S. Pat. No. 9,155,619, which is incorporated herein by reference.

FIG. 17 shows an example of a prosthetic implant delivery assembly 200, according to another embodiment. The delivery assembly 200 can comprise two main components: a prosthetic heart valve 202 and a delivery apparatus 204. The prosthetic valve 202 can be releasably coupled to the delivery apparatus 204, as further described below.

The prosthetic valve 202 can have an annular stent or frame 206. Although the frame 202 of the prosthetic valve 202 is annular, for purposes of illustration, only a partial annular portion of the frame 206 is shown for clarity. Also, although the prosthetic valve 202 can also have a valve structure disposed radially within and coupled to the frame 206 (e.g., in a manner similar to the prosthetic valve 102), for purposes of illustration, the valve structure of the prosthetic valve 202 is not shown for clarity.

The frame 206 of the prosthetic valve 202 can have an inflow end portion 208, and intermediate portion 210, and an outflow end portion 212. The frame 206 can also have a plurality of interconnected struts 214 arranged in a lattice-type pattern and forming a plurality of apices 216, 218 at the respective ends 210, 214 of the frame 206.

Figure 23:
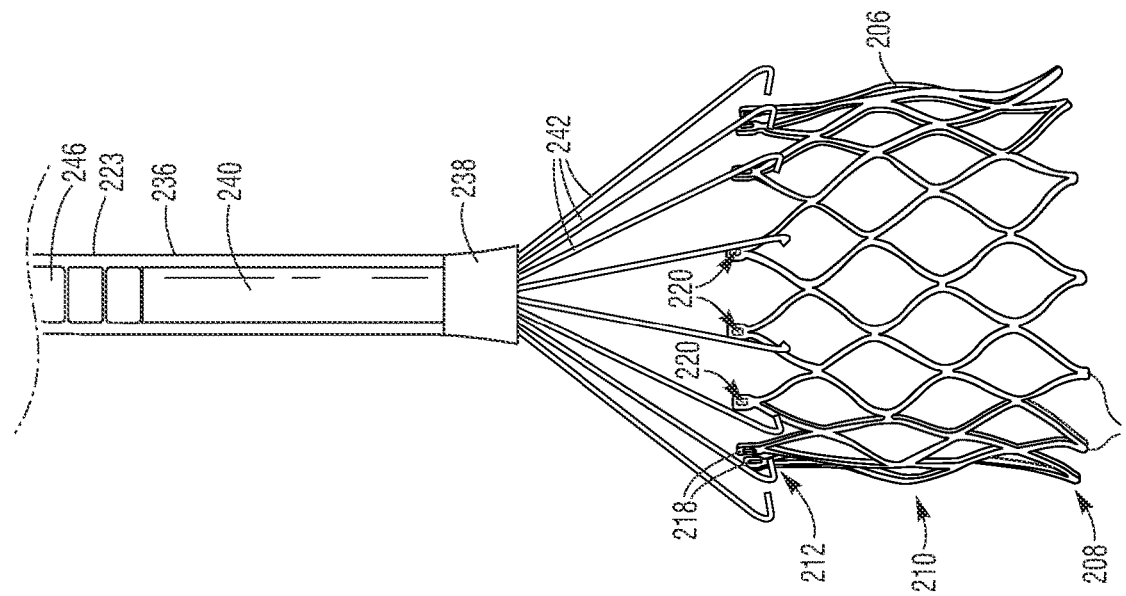

At least some of the apices 218 at the outflow end 212 of the frame 206 can have a respective aperture or opening 220 formed therein, as best shown in FIG. 23. For example, in the illustrated embodiment, all of the apices 218 have an opening 220 formed therein. In other embodiments, fewer than all of the apices 218 have openings 220 formed therein. For example, one half, one third, or one fourth of the apices 218 can have openings 220 formed therein. In such embodiments, the apices 218 have the openings 220 can be uniformly distributed circumferentially around the outflow end 212 of the frame 206 (e.g., symmetrically—in an alternating type pattern).

The openings 220 in the apices 218 can comprise various shapes. For example, the openings 220 can be generally rectangular, circular, ovular, etc. The openings 220 can be sized such that the openings 220 can releasably coupled receive to the delivery apparatus 204, as further explained below (see, e.g., FIG. 18).

The frame 206 can be made of any of various suitable plastically-expandable materials (e.g., stainless steel, etc.) or self-expanding materials (e.g., nickel titanium alloy ("NiTi"), such as Nitinol) as known in the art. When constructed of a plastically-expandable material, the frame 206 (and thus the prosthetic valve 202) can be crimped to a radially collapsed configuration or state on a delivery catheter and then expanded inside a patient by an inflatable balloon or equivalent expansion mechanism to a functional state. When constructed of a self-expandable material, the frame 206 (and thus the prosthetic valve 202) can be crimped to a radially collapsed configuration (see, e.g., FIG. 19) and restrained in the collapsed configuration by insertion into a sheath or equivalent mechanism of a delivery catheter. Once inside the body, the prosthetic valve can be advanced from the delivery sheath, which allows the prosthetic valve to radially expand to its functional state (e.g., FIGS. 19-23).

The delivery apparatus 204 can comprise a handle (not shown), an outer catheter 222 and an implant delivery catheter 224. The handle can be disposed adjacent to a proximal end portion of the delivery apparatus 204. The outer catheter 222 and the implant delivery catheter 224 can extend coaxially from the proximal end of the delivery apparatus 104 toward an opposite, distal end portion 230 of the delivery apparatus 204. The implant delivery catheter 224 can be disposed radially within and extend axially through a lumen 232 (FIG. 18) of the outer catheter 222.

Although the implant delivery catheter 224 is disposed radially within the outer catheter 222, for purposes of illustration, the outer catheter 222 is shown as transparent (except in FIG. 19) to better show the implant delivery catheter 224.

The outer catheter 222 and the implant delivery catheter 224 can each be independently moveable relative to each other. In some embodiments, the delivery apparatus 204 can be configured such that relative axial movement between the outer and implant delivery catheters 222, 224 at or near the proximal end of the delivery apparatus 204 can cause corresponding relative axial movement at or near the distal end 230 of the delivery apparatus 204. For example, the delivery apparatus 204 can be configured such that axially advancing a proximal end of the implant delivery catheter 224 in the distal direction while maintaining the axial positioning of the outer catheter 222 causes a distal end of the implant delivery catheter 224 to axially advance in the distal direction relative to the outer catheter 222.

In an alternative embodiment, the delivery apparatus 204 can be configured such that relative rotational movement between the outer and implant delivery catheters 222, 224 at or near the proximal end of the delivery apparatus 204 can cause corresponding relative rotational movement at or near the distal end 230 of the delivery apparatus 204. For example, the delivery apparatus 204 can be configured such that rotating the proximal end of the implant delivery catheter 224 in a first direction while preventing rotational movement of the outer catheter 222 causes the distal end of the implant delivery catheter 224 to rotate in the first direction relative to the outer catheter 222.

Figure 19:
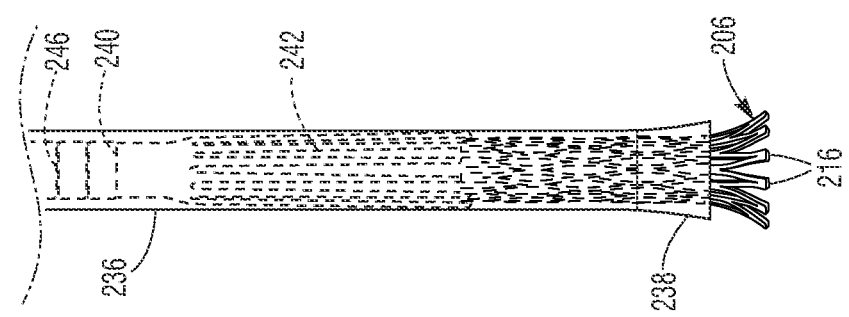

The outer catheter 222 can have a shaft portion 223 having a distal end portion comprising a sheath portion 236. The sheath 236 can be used to retain the prosthetic valve 104 in a radially compressed state, as best shown in FIG. 19. The sheath 236 of the outer catheter 222 can comprise a tip portion 238 disposed at a distal end of the sheath 236.

Figure 21:
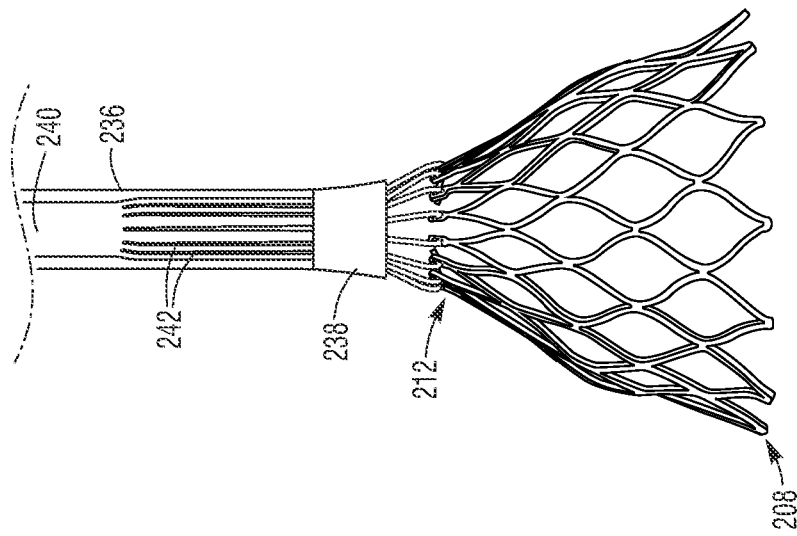
FIGS. 19-23 are perspective views of various configurations of the prosthetic implant delivery assembly of FIG. 17.

Referring now to FIG. 21, the implant delivery catheter 224 can comprise a shaft 240 and a plurality of tines or arms 242. The arms 242 of the implant delivery catheter 224 can extend axially from a distal end 244 of the shaft 240 and can be spaced apart circumferentially relative to each other. Although the illustrated embodiment shows eight arms, other embodiments can have less or more arms. For example, the implant delivery catheter 224 can have 2-20 arms, 5-16 arms, or 12-15 arms.

Referring now to FIG. 23, the shaft 240 of the implant delivery catheter 224 can have a plurality of circumferentially extending slots 246 formed in one or more sides of the shaft 240. Similar to the slots 154 of the release catheter 126" of the delivery assembly 100, the slots 246 can improve the flexibility of the implant delivery catheter 224 and can be configured to cause the implant delivery catheter to bend relatively more easily toward one side of the implant delivery catheter 224 than toward another side of the implant delivery catheter 224.

The arms 242 of the implant delivery catheter 224 can each have a curved or hook portion 246 disposed at a distal end a respective arm 242. The hooks 246 can extend radially inward and can be used to releasably couple the prosthetic valve 202 to the delivery apparatus 204. For example, referring now to FIG. 18, the hooks 246 can be configured so that the hooks 246 extend radially through respective openings 220 of the apices 218 of the prosthetic valve 202, thereby releasably coupling the prosthetic valve 202 to the delivery apparatus 204 via the implant delivery catheter 224, as further described below.

Figure 25:
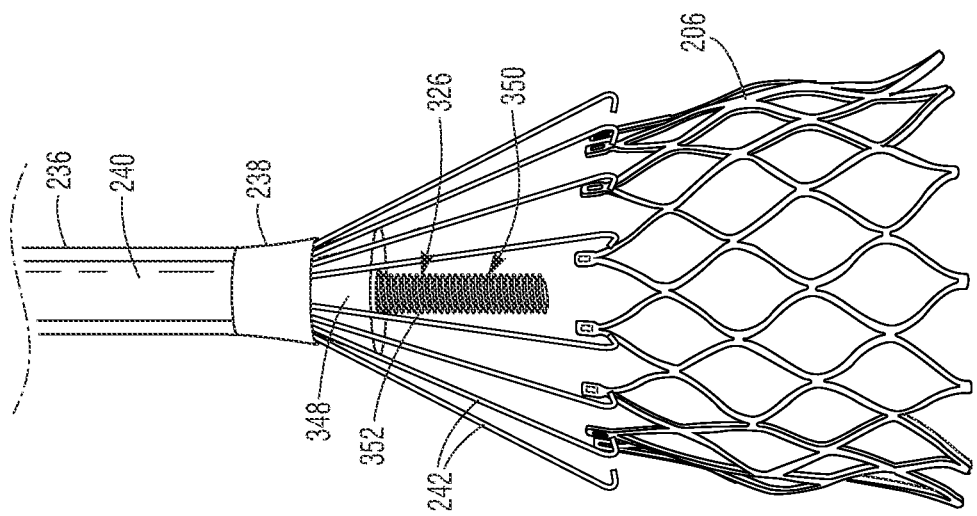
FIGS. 24-25 are perspective views of another embodiment of a prosthetic implant delivery assembly.

The arms 242 of the implant delivery catheter 224 can be configured to be radially expandable from a radially compressed state (e.g., FIGS. 19-20) to radially expanded state (e.g., FIGS. 23, 25). This can be accomplished, for example, by forming the arms 242 from any of various suitable self-expanding materials (e.g., nickel titanium alloy ("NiTi"), such as Nitinol). The arms 242 can, for example, be formed by laser-cutting a Nitinol tube and shape-setting the arms 242 in the radially expanded state.

When constructed of a self-expandable material, the arms 242 of the implant delivery catheter 224 can be radially compressed by retracting the implant delivery catheter 224 relative to the outer catheter 222 or by advancing the outer catheter 222 relative to the implant delivery catheter 224 such that the arms 242 are disposed with the sheath 236 of the outer catheter 222. The arms 242 can be radially expanded by advancing the implant delivery catheter 224 relative to the outer catheter 222 or by retracting the outer catheter 222 relative to the implant delivery catheter 224 such that the arms 242 are exposed from the sheath 236 of the outer catheter 222.

As best shown in FIG. 18, the arms 242 can be configured to have a release point 254. At the release point 254, the arms 242 can be radially tapered or angled relative to the distal end portions of the arms so as to allow the arms 242 to expand radially outward to the extent that the hooks 246 disengage from the openings 220 of the prosthetic valve 202 when the release point 254 is exposed from the sheath 236 of the outer catheter 222.

In some embodiments, each of the hooks 246 of the arms 242 can extend radially inwardly and can be angled at least slightly proximally. As such, the hooks 246 can be configured such that when the arms 242 expand from the radially compressed state to the radially expanded state the proximal angle of the hooks 246 increases relative to the openings 220 of the frame 206. Stated another way, the hooks 246 can be configured so as to engage the apices 218 of the frame 206 relatively more when the arms 242 are in the radially compressed state (to facilitate interlocking between the arms 242 and the frame 206) than when the arms 242 are in the radially expanded state (to facilitate disengaging between the arms 242 and the frame 206).

In this manner, the delivery apparatus 204 can be used to percutaneously deliver and position the prosthetic valve 202 in a native annulus of a heart. The prosthetic valve 202 can be releasably coupled to the delivery apparatus 204 by positioning the hooks 246 of the implant delivery catheter 224 into the openings 220 in the frame 206 of the prosthetic valve 202. The prosthetic valve 202 and the arms 242 of the implant delivery catheter 224 can be radially compressed or crimped and retained in their respective compressed configurations by positioning the prosthetic valve 202 and the arms 242 of the implant delivery catheter 224 within the sheath 236 of the outer catheter. The delivery apparatus 204 and thus the prosthetic valve 202 can then be inserted into a patient's body and advanced to a desired native annulus of the patient's heart (e.g., a native aortic annulus).

Figure 20:
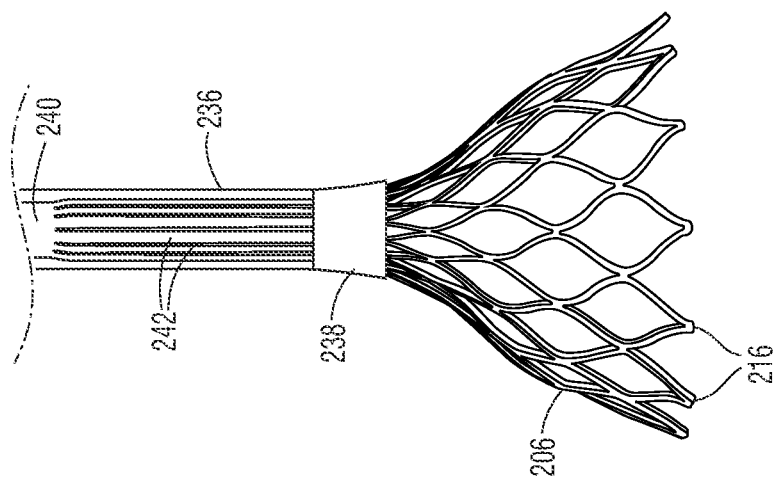
Figure 22:
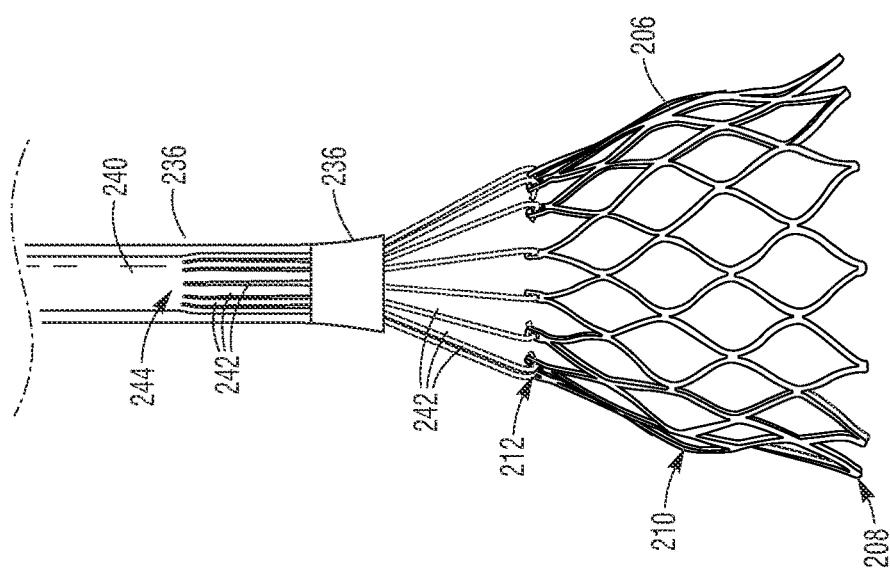

Once the delivery apparatus 204 and the prosthetic valve 202 are desirably positioned in the native annulus, the prosthetic valve 202 can be deployed by retracting the outer catheter 222 proximally relative to the implant delivery catheter 224 (or by advancing the implant delivery catheter 224 distally relative to the outer catheter 222). As the prosthetic valve 202 is exposed from the sheath 236, the prosthetic valve 202 begins radially expanding, as shown in FIGS. 19-20. Retracting the outer catheter 222 proximally farther allows the arms 242 of the implant delivery catheter 224 and thus the outflow end 212 of the prosthetic valve 202 to expand, as shown in FIGS. 21-22.

The prosthetic valve 202 can be positioned and/or repositioned, for example, by moving the implant delivery catheter 224. The prosthetic valve 202 can also be partially and/or fully recompressed by retracting the implant delivery catheter 224 proximally relative to the outer catheter 222 (or by advancing the outer catheter 222 distally relative to the implant delivery catheter 224), thus allowing the prosthetic valve 202 to be repositioned and redeployed and/or retrieved from the patient's body.

Once the prosthetic valve 202 is desirably positioned and secured with the native annulus, the sheath 236 can be retracted proximally relative to the implant delivery catheter 224 such that the release point 254 (FIG. 18) of the arms 242 is exposed from the sheath 236. This allows the arms 242 to fully expand radially outward to the extent that the hooks 246 retract from within the openings 220 of the prosthetic valve 202, thereby releasing the prosthetic valve 202 from the delivery apparatus 204, as shown in FIG. 23.

Figure 24:
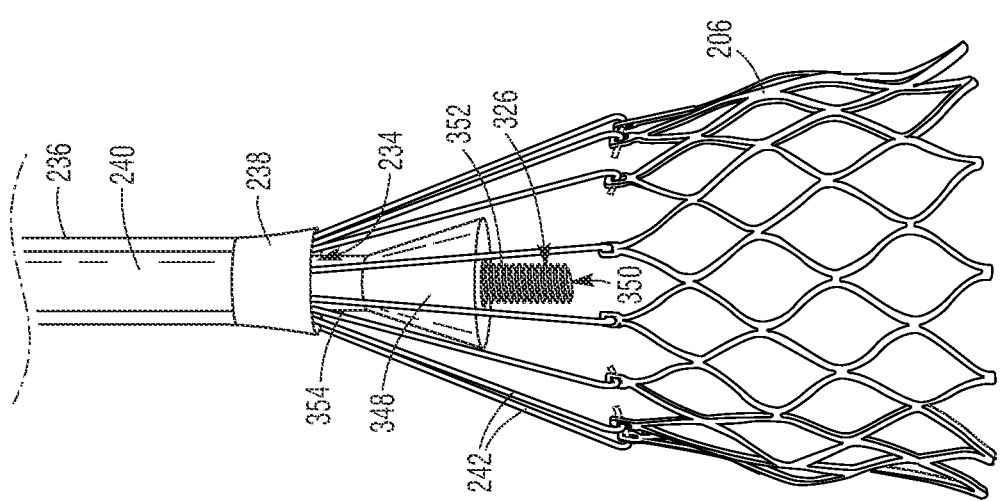

Referring now to FIGS. 24-25, in some embodiments, the delivery apparatus 204 can have an inner catheter 326 having an expansion element 348. The inner catheter 326 can be dispose radially within and extend axially through a lumen 234 (FIG. 24) of the implant delivery catheter 224 (which is an intermediate catheter in this embodiment) and can be independently moveable (e.g., axially slidable/translatable or rotatable) relative to the outer and implant delivery catheters 222, 224.

The expansion element 348 can be coupled to a distal end 350 the inner catheter 326. The expansion element 348 can have a generally frusto-conical shape. As such, the expansion element 348 can be used to assist and/or to cause radially expansion of the arms 242 of the implant delivery catheter 224. For example, when the arms 242 of the implant delivery catheter 224 are exposed from the sheath 236 of the outer catheter 222, the expansion element 348 can be retracted proximally relative to the implant delivery catheter 224 such that the expansion element 348 contacts the arms 242 and thus forces the arms 242 to expand radially outward.

The expansion element 348 can provide several significant advantages. For example, the expansion element 348 can be used to release the prosthetic valve 202 from the delivery apparatus 204 in the event that the self-expanding force of the arms 242 of implant delivery catheter 224 is insufficient to cause the arms 242 to radially expand enough to remove the hooks 246 from the openings 220 of the prosthetic valve 202. This can be particularly useful when, for example, a patient's native anatomy interferes with and thus prevents the arms 242 from fully expanding.

The expansion element 348 can also allow the arms 242 to be formed from suitable plastically-expandable materials (e.g., stainless steel, etc.) because the expansion element 348 can be used to expand the arms 242.

In some embodiments, the expansion element 348 can be fixedly coupled to the inner catheter 326. As such, relative axial motion between the expansion member 348 and the arms 242 of the implant delivery catheter 224 can be caused by pushing the inner catheter 326 distally or pulling the inner catheter proximally relative to the implant delivery catheter 224, which in turn causes the expansion member 348 to respectively advance distally or retract proximally relative to the arms 242.

In other embodiments, the expansion element 348 can be slidably coupled to the inner catheter 326. For example, in some embodiments, rotating the inner catheter 326 relative to the expansion element 348 in first direction causes the expansion element 348 to slide or translate proximally along the inner catheter 326 and into contact with the arms 242 of the implant delivery catheter 224, and rotating the inner catheter 326 relative to the expansion element 348 in second, opposite direction causes the expansion element 348 to slide or translate distally along the inner catheter 326 and away from the arms 242 of the implant delivery catheter 224. This can be accomplished, for example, by forming the inner catheter 326 with external threads 352, by forming the expansion element 348 with corresponding internal threads (not shown), and by preventing the expansion element 348 from rotating together with the inner catheter 326, such as by slidably attaching or connecting the expansion element 348 to another component of the delivery apparatus (e.g., the outer catheter 222, the shaft 240, and/or the arms 242) by a shaft or sleeve 354. In other embodiments, the outer surface of the expansion element 348 can, for example, be formed with longitudinal slots (not shown) that receive the arms 242. As such, the arms 242 are allowed to slide axially relative to the slots, but the slots prevent rotation of the expansion element 348 when the inner shaft 326 is rotated.

The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

What is claimed is:

1. A prosthetic implant delivery assembly comprising:
a prosthetic implant comprising an expandable stent, the expandable stent comprising a plurality of interconnected struts and a plurality of apices circumferentially spaced around a first end portion of the expandable stent, each of the plurality of apices formed by a junction of a pair of the plurality of struts, wherein at least some of the plurality of apices comprise an aperture formed therein; and
an elongate catheter comprising a shaft, a plurality of arms extending axially from a distal end portion of the shaft, a sheath disposed radially outwardly from the shaft, and an expansion element disposed radially inwardly from the sheath, the plurality of arms being radially expandable relative to a longitudinal axis of the shaft and configured to be moveable from a radially compressed state to a radially expanded state via relative movement between the plurality of arms and the sheath, each arm of the plurality of arms comprising a hook portion, wherein the hook portion of each of the plurality of arms is configured to releasably engage one of the at least some of the plurality of apices of the prosthetic implant via the aperture,
wherein the plurality of arms is configured to move from the radially compressed state to the radially expanded state when the plurality of arms is exposed from within the sheath such that the hook portion of each of the plurality of arms disengages from the one of the at least some of the plurality of apices of the prosthetic implant and releases the expandable stent from the elongate catheter, and
wherein the expansion element has a frusto-conical shape and is configured to be retracted toward the distal end portion of the shaft, and wherein the expansion element is movable relative to the plurality of arms and is configured to apply a radial force to the plurality of arms to cause the radial expansion thereof as the expansion element is retracted.

2. The prosthetic implant delivery assembly of claim 1, wherein the hook portion of each of the plurality of arms extends radially inwardly and is angled proximally.

3. The prosthetic implant delivery assembly of claim 2, wherein the elongate catheter is configured such that, while the hook portion of each of the plurality of arms is engaged with the respective one of the at least some of the plurality of apices of the prosthetic implant and while the plurality of arms is in the radially compressed state, a distal angle of the hook portion relative to a longitudinal axis of the expandable stent is less than 90 degrees.

4. The prosthetic implant delivery assembly of claim 3, wherein the elongate catheter is configured such that, while the hook portion of each of the plurality of arms is engaged with the one of the at least some of the plurality of apices of the prosthetic implant, the distal angle of the hook portion relative to the longitudinal axis of the expandable stent increases as the plurality of arms is moved from the radially compressed state toward the radially expanded state.

5. The prosthetic implant delivery assembly of claim 1, wherein the elongate catheter is configured such that an extent of radial expansion of the plurality of arms is adjustable, wherein movement of the sheath relative to the plurality of arms in a first direction causes the plurality of arms to be retracted into the sheath and decreases the extent of radial expansion of the plurality of arms, and wherein movement of the sheath relative to the plurality of arms in an opposing second direction causes the plurality of arms to be exposed from the sheath and increases the extent of radial expansion of the plurality of arms.

6. The prosthetic implant delivery assembly of claim 1, wherein each arm of the plurality of arms further comprises a distal portion and a release point structure, the release point structure disposed at an opposing end of the distal portion relative to the hook portion and comprising a section of the arm that is angled relative to the distal portion.

7. The prosthetic implant delivery assembly of claim 6, wherein each arm of the plurality of arms further comprises a proximal portion, and wherein the release point structure is disposed between the distal portion and the proximal portion, the section of the arm being angled relative to the proximal portion.

8. The prosthetic implant delivery assembly of claim 6, wherein the elongate catheter is configured such that, in the radially compressed state, the distal portion of each of the plurality of arms is abutted to an interior surface of the sheath and a space is disposed between the interior surface of the sheath and the release point structure of each of the plurality of arms.

9. The prosthetic implant delivery assembly of claim 6, wherein the elongate catheter is configured such that movement of the plurality of arms into the radially expanded state is caused at least in part by exposure of the release point structure from the sheath for each of the plurality of arms.

10. The prosthetic implant delivery assembly of claim 9, wherein the elongate catheter is configured such that the exposure of the release point structure from the sheath results in an increase of a proximal angle of the hook portion relative to a proximal region of the aperture and disengagement of the hook portion of each of the plurality of arms from the aperture of the one of the at least some of the plurality of apices.

11. The prosthetic implant delivery assembly of claim 1, wherein the expandable stent is a self-expandable stent and the plurality of arms is a self-expandable plurality of arms.

12. A prosthetic implant delivery assembly comprising:
a prosthetic implant comprising an expandable stent having a plurality of apices circumferentially spaced around a first end portion of the expandable stent, wherein each of at least some of the plurality of apices comprises an aperture;
a sheath configured to receive the prosthetic implant therein and to retain the prosthetic implant in a radially compressed configuration;
an elongate first catheter comprising a first shaft and an expansion element movably coupled to a distal end portion of the first shaft; and
an elongate second catheter comprising a second shaft and a plurality of arms extending axially from a distal end portion of the second shaft, the plurality of arms being radially expandable relative to a longitudinal axis of the second shaft and configured to be moveable from a radially compressed state to a radially expanded state via relative axial movement between the plurality of arms and the sheath, each arm of the plurality of arms comprising a hook portion, wherein the hook portion of each of the plurality of arms extends radially inwardly and is angled proximally, and wherein the hook portion of each of the plurality of arms is configured to extend through a respective aperture of the at least some of the plurality of apices to releasably couple the prosthetic implant to the elongate second catheter,
wherein the plurality of arms is configured to radially expand when the plurality of arms is exposed from within the sheath, and
wherein the expansion element is configured to be moved proximally relative to the first shaft and toward the distal end portion of the second shaft such that the expansion element applies a radial force to the plurality of arms to release the prosthetic implant from the elongate second catheter.

13. The prosthetic implant delivery assembly of claim 12, wherein the elongate second catheter is configured such that, when the hook portion of each of the plurality of arms extends through the respective aperture and when the plurality of arms is in the radially compressed state, a distal angle of the hook portion relative to a longitudinal axis of the expandable stent is less than 90 degrees.

14. The prosthetic implant delivery assembly of claim 13, wherein the elongate second catheter is configured such that the distal angle of the hook portion relative to the longitudinal axis of the expandable stent increases as the plurality of arms is moved from the radially compressed state toward the radially expanded state.

15. A prosthetic implant delivery assembly comprising:
a prosthetic implant comprising an expandable stent having a plurality of apices circumferentially spaced around a first end portion of the expandable stent, wherein each of at least some of the plurality of apices comprises an aperture; and
a delivery apparatus comprising a first shaft a second shaft, and a third shaft, each being axially movable relative to each other, the first shaft including a plurality of arms disposed at a distal end portion of the first shaft, the second shaft including a sheath disposed at a distal end portion of the second shaft, the plurality of arms being radially expandable from a radially compressed state to a radially expanded state via relative movement between the plurality of arms and the sheath, each arm of the plurality of arms comprising a hook portion, wherein the hook portion of each of the plurality of arms is configured to extend through the aperture of one of the at least some of the plurality of apices, and wherein each arm of the plurality of arms further comprises a distal portion and a release point structure, the release point structure disposed at an opposing end of the distal portion relative to the hook portion and comprising a section of the arm that is angled relative to the distal portion, the third shaft including an expansion element disposed on a distal end portion of the third shaft,
wherein the plurality of arms is configured to radially expand from the radially compressed state toward the radially expanded state as the plurality of arms is exposed from within the sheath, and wherein, in the radially expanded state, the hook portion of each of the plurality of arms withdraws from the aperture of the one of the at least some of the plurality of apices to release the expandable stent from the delivery apparatus, and wherein the expansion element is configured to be moved proximally relative to the first shaft and the second shaft, which results in the expansion element applying a radial force to the plurality of arms to release the prosthetic implant from the delivery apparatus.

16. The prosthetic implant delivery assembly of claim 15, wherein each arm of the plurality of arms further comprises a proximal portion, and wherein the release point structure is disposed between the distal portion and the proximal portion, the section of the arm being angled relative to the proximal portion.

17. The prosthetic implant delivery assembly of claim 15, wherein the delivery apparatus is configured such that, in the radially compressed state, the distal portion of each of the plurality of arms is abutted to an interior surface of the sheath and a space is disposed between the interior surface of the sheath and the release point structure of each of the plurality of arms.

18. The prosthetic implant delivery assembly of claim 15, wherein the delivery apparatus is configured such that movement of the plurality of arms into the radially expanded state is caused at least in part by exposure of the release point structure from the sheath for each of the plurality of arms.

19. The prosthetic implant delivery assembly of claim 18, wherein the delivery apparatus is configured such that the exposure of the release point structure from the sheath results in increase of a proximal angle of the hook portion relative to a proximal region of the aperture and disengagement of the hook portion from the aperture of the one of the at least some of the plurality of apices.

* * * * *